US007226596B2

(12) United States Patent
Bodary et al.

(10) Patent No.: US 7,226,596 B2
(45) Date of Patent: Jun. 5, 2007

(54) COMPOSITIONS AND METHODS FOR THE TREATMENT OF TUMORS

(75) Inventors: Sarah C. Bodary, San Bruno, CA (US); Karen L. Fisher, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 281 days.

(21) Appl. No.: 10/226,844

(22) Filed: Aug. 22, 2002

(65) Prior Publication Data

US 2003/0113764 A1 Jun. 19, 2003

Related U.S. Application Data

(63) Continuation of application No. 09/627,202, filed on Jul. 27, 2000, now abandoned.

(60) Provisional application No. 60/146,217, filed on Jul. 28, 1999.

(51) Int. Cl.
*A61K 39/00* (2006.01)
(52) U.S. Cl. .............................. 424/181.1; 424/178.1; 424/183.1; 424/133.1; 424/134.1; 424/135.1; 424/138.1; 424/155.1; 530/350; 530/387.1; 530/387.3; 530/387.7; 530/388.8; 530/391.3; 530/391.7
(58) Field of Classification Search ............. 424/174.1, 424/181.1, 133.1, 135.1, 138.1, 155.1, 178.1, 424/134.1; 242/183.1; 530/350, 387.7, 530/391.3, 391.7, 388.8, 387.1, 387.3
See application file for complete search history.

(56) References Cited

U.S. PATENT DOCUMENTS

| 5,859,253 | A | * | 1/1999 | Beckett et al. .............. 546/306 |
| 6,156,321 | A | | 12/2000 | Thorpe et al. |
| 6,458,552 | B1 | * | 10/2002 | Fourie et al. ................. 435/23 |
| 2003/0166562 | A1 | * | 9/2003 | Rothenberg et al. .......... 514/12 |

FOREIGN PATENT DOCUMENTS

WO    WO 97/40072        10/1997
WO    WO 0109189 A   *   2/2001

OTHER PUBLICATIONS

Chen et al. Mol. Cell. Proteomics. Apr. 2002; 1 (4): 304-13.*
Liu et al. Cancer J. Sep.-Oct. 2001; 7 (5): 395-403.*
Jiang et al. J. Biol. Chem. Feb. 11, 2005; 280 (6): 4656-62.*
Rae et al. International Journal of Cancer. 2000; 88: 726-32.*
De Plaen et al. Immunogenetics. 1994; 40: 360-9.*
Skolnick et al. Trends in Biotechnology 2000; 18: 34-9.*
Saijo et al. Cancer Sci. Oct. 2004; 95 (10): 772-6.*
Kelland Eur. J. Cancer. Apr. 2004; 40 (6): 827-36.*
Amour et al. FEBS Lett. Jul. 31, 2002; 524 (1-3): 154-8.*
Lendeckel et al. (J Cancer Res Clin Oncol. Jan. 2005;131(1):41-8).*
Ishikawa et al. (Clin Cancer Res. Dec. 15, 2004;10(24):8363-70)*
Alitalo et al., "Oncogene Amplification in Tumor Cells", *Advances in Cancer Research*, vol. 47, pp. 235-281 (1986).
Baselga et al., "HER2 Overexpression and Paclitaxel Sensitivity in Breast Cancer: Therapeutic Implications", *Oncology*, vol. 11 (3 Suppl. 2). pp. 43-48 (Mar. 1997).
Baselga et al., "Phase II Study of Weekly Intravenous Recombinant Humanized Anti-p185$^{HER2}$ Monoclonal Antibody in Patients with HER2/neu-Overexpressing Metastatic Breast Cancer", *J. Clin. Oncol.*, vol. 14, No. 3, pp. 737-744 (Mar. 1996).
Bergers, G. et al., "Extrinsic Regulators of Epithelial Tumor Progression: Metalloproteinases", *Current Opinion in Genetics and Development*, vol. 10, pp. 120-127 (2000).
Bishop, J., "Molecular Themes in Oncogenesis", *Cell*, vol. 64, No. 2, pp. 235-248 (Jan. 25, 1991).
Bodey, B. et al., "Failure of Cancer Vaccines: The Significant Limitations of this Approach to Immunotherapy", *Anticancer Research*, vol. 20, pp. 2665-2676, (2000).
Brown, P., "Matrix Metalloproteinase Inhibitors in the Treatment of Cancer", *Medical Oncology*, vol. 14, pp. 1-10 (1997).
Curti, B., "Physical Barriers to Drug Delivery in Tumors", *Critical Reviews in Hematology/Oncology*, vol. 14, pp. 29-39 (1993).
DeNardo, G. et al., "Strategies for Developing Effective Radioimmunotherapy for Solid Tumors", *Clinical Caner Research*, vol. 5, pp. 3219s-3223s (1999).
Gura, T., "Systems for Identifying Drugs are Often Faulty", *Science*, vol. 278, pp. 1041-1042 (1997).
Higuchi et al., "MS2 (ADAM 8) A Myelomonolytic Cell Surface Antigen: Expression, Chromosomal Localization and Production of Truncated ADAM 8 Transgenic Mice", *Tissue Antigens*, vol. 48, p. 423 (1996).
Hunter, T., "Cooperation Between Oncogenes", *Cell*, vol. 64, No. 2, pp. 249-270 (Jan. 25, 1991).
Hynes et al., "The Biology of erbB-2/neu/HER-2 and Its Role in Cancer", *Biochimica et Biophysica Acta*, vol. 1198, No. 2-3, pp. 165-184 (Dec. 30, 1994).
Jain. R., "Barriers to Drug Delivery in Solid Tumors", *Scientific American*, vol. 271, pp. 58-65 (1994).
Kataoka et al., "Structure of Murine CD156 Gene, Characterization of Its Promoter, and Chromosomal Location", *Journal of Biological Chemistry*, vol. 29, pp. 18209-18215 (1997).
Lewis, G. et al., "Differential Responses of Human Tumor Cell Lines to anti- p185HER2 Monoclonal Antibodies", *Cancer Immunology, Immunotherapy*, vol. 37, pp. 255-263 (1993).
Ravdin et al., "The c-erbB-2 proto-oncogene as a Prognostic and Predictive Marker in Breast Cancer: A Paradigm for the Development of Other Macromolecular Markers—A Review", *Gene*, vol. 159, No. 1, pp. 19-27 (Jun. 14, 1995).

(Continued)

*Primary Examiner*—Stephen L. Rawlings
(74) *Attorney, Agent, or Firm*—Merchant & Gould P.C.

(57) ABSTRACT

The invention concerns compositions and methods for the diagnosis and treatment of neoplastic cell growth and proliferation in mammals, including humans. The invention is based upon the identification of an ADAM8 gene that is amplified in the genome of tumor cells. Such gene amplification is associated with the overexpression of the gene product as compared to normal cells of the same tissue type and contributes to tumorigenesis. Accordingly, the ADAM8 protein encoded by the amplified gene is a useful target for the diagnosis and/or treatment (including prevention) of certain cancers, and acts as a predictor of the prognosis of tumor treatment.

12 Claims, No Drawings

OTHER PUBLICATIONS

Schluesener, H., "The Disintegrin Domain of ADAM 8 Enhances Protection Against Rat Experimental Autoimmune Encephalomyelitis, Neuritis and Uveitis by a Polyvalent Autoantigen Vaccine", *Journal of Neuroimmunology*, vol. 87, pp. 197-202 (1998).

Schwab et al., "Amplification of Cellular Oncogenes: A Predictor of Clinical Outcome in Human Cancer", *Genes, Chromosomes & Cancer*, vol. 1, No. 3, pp. 181-193 (Jan. 1990).

Slamon et al., "Human Breast Cancer: Correlation of Relapse and Survival with Amplification of the HER-2/neu Oncogene", *Science*, vol. 235, pp. 177-182 (Jan. 9, 1987).

Slamon et al., "Studies of the HER-2/neu Proto-oncogene in Human Breast and Ovarian Cancer", *Science*, vol. 244, pp. 707-712 (May 12, 1989).

Stancovski, I. et al., "Mechanistic Aspects of the Opposing Effects of Monoclonal Antibodies to theERBB2 Receptor on Tumor Growth", *Proceedings of the National Academy of Science USA*, vol. 88, pp. 8691-8695 (1991).

Vitetta, E. et al., "Monoclonal Antibodies as Agonists: An Expanded Role for Their Use in Cancer Therapy", *Cancer Research*, vol. 54, pp. 5301-5309 (1994).

Yamamoto et al., "ADAM Family Proteins in the Immune System", *Immunology Today*, vol. 20, No. 6, pp. 278-284 (1999).

Yamamoto et al., "Human MS2 Antigen: Molecular Cloning, Primary Amino Acid Sequence, and Tissue Distribution", *Leukocyte Typing V: White Cell Differentiation Antigens*, (Proceedings of the Fifth International Workshop and Conf.), Schlossman et al., Oxford Univ. Press, pp. 1091-1093 (1995).

Yoshida et al., "Molecular Cloning on cDNA Encoding MS2 Antigen, a Novel Cd Surface Antigen Strongly Expressed in Murine Monolytic Lineage", *International Immunology*, vol. 2, pp. 585-591 (1990).

Yoshiyama et al., "CD156 (Human ADAM8): Expression, Primary Amino Acid Sequence, and Gene Location",*Genomics*, vol. 41, pp. 56-62 (1997).

\* cited by examiner

SEQUENCE LISTING

<160> NUMBER OF SEQ ID NOS: 22

<210> SEQ ID NO 1
<211> LENGTH: 824
<212> TYPE: PRT
<213> ORGANISM: Homo sapien

<400> SEQUENCE: 1

Met Arg Gly Leu Gly Leu Trp Leu Leu Gly Ala Met Met Leu Pro
 1               5                  10                  15

Ala Ile Ala Pro Ser Arg Pro Trp Ala Leu Met Glu Gln Tyr Glu
                20                  25                  30

Val Val Leu Pro Arg Arg Leu Pro Gly Pro Arg Val Arg Arg Ala
                35                  40                  45

Leu Pro Ser His Leu Gly Leu His Pro Glu Arg Val Ser Tyr Val
                50                  55                  60

Leu Gly Ala Thr Gly His Asn Phe Thr Leu His Leu Arg Lys Asn
                65                  70                  75

Arg Asp Leu Leu Gly Ser Gly Tyr Thr Glu Thr Tyr Thr Ala Ala
                80                  85                  90

Asn Gly Ser Glu Val Thr Glu Gln Pro Arg Gly Gln Asp His Cys
                95                  100                 105

Leu Tyr Gln Gly His Val Glu Gly Tyr Pro Asp Ser Ala Ala Ser
                110                 115                 120

Leu Ser Thr Cys Ala Gly Leu Arg Gly Phe Phe Gln Val Gly Ser
                125                 130                 135

Asp Leu His Leu Ile Glu Pro Leu Asp Glu Gly Gly Glu Gly Gly
                140                 145                 150

Arg His Ala Val Tyr Gln Ala Glu His Leu Leu Gln Thr Ala Gly
                155                 160                 165

Thr Cys Gly Val Ser Asp Asp Ser Leu Gly Ser Leu Gly Pro
                170                 175                 180

Arg Thr Ala Ala Val Phe Arg Pro Arg Pro Gly Asp Ser Leu Pro
                185                 190                 195

Ser Arg Glu Thr Arg Tyr Val Glu Leu Tyr Val Val Val Asp Asn
                200                 205                 210

Ala Glu Phe Gln Met Leu Gly Ser Glu Ala Ala Val Arg His Arg
                215                 220                 225

Val Leu Glu Val Val Asn His Val Asp Lys Leu Tyr Gln Lys Leu
                230                 235                 240

Asn Phe Arg Val Val Leu Val Gly Leu Glu Ile Trp Asn Ser Gln
                245                 250                 255

Asp Arg Phe His Val Ser Pro Asp Pro Ser Val Thr Leu Glu Asn
                260                 265                 270

Leu Leu Thr Trp Gln Ala Arg Gln Arg Thr Arg Arg His Leu His
                275                 280                 285

Asp Asn Val Gln Leu Ile Thr Gly Val Asp Phe Thr Gly Thr Thr
                290                 295                 300

Val Gly Phe Ala Arg Val Ser Ala Met Cys Ser His Ser Ser Gly
                305                 310                 315

Ala Val Asn Gln Asp His Ser Lys Asn Pro Val Gly Val Ala Cys
                320                 325                 330

Thr Met Ala His Glu Met Gly His Asn Leu Gly Met Asp His Asp

-continued

```
                335                 340                 345
Glu Asn Val Gln Gly Cys Arg Cys Gln Glu Arg Phe Glu Ala Gly
                350                 355                 360
Arg Cys Ile Met Ala Gly Ser Ile Gly Ser Ser Phe Pro Arg Met
                365                 370                 375
Phe Ser Asp Cys Ser Gln Ala Tyr Leu Glu Ser Phe Leu Glu Arg
                380                 385                 390
Pro Gln Ser Val Cys Leu Ala Asn Ala Pro Asp Leu Ser His Leu
                395                 400                 405
Val Gly Gly Pro Val Cys Gly Asn Leu Phe Val Glu Arg Gly Glu
                410                 415                 420
Gln Cys Asp Cys Gly Pro Pro Glu Asp Cys Arg Asn Arg Cys Cys
                425                 430                 435
Asn Ser Thr Thr Cys Gln Leu Ala Glu Gly Ala Gln Cys Ala His
                440                 445                 450
Gly Thr Cys Cys Gln Glu Cys Lys Val Lys Pro Ala Gly Glu Leu
                455                 460                 465
Cys Arg Pro Lys Lys Asp Met Cys Asp Leu Glu Glu Phe Cys Asp
                470                 475                 480
Gly Arg His Pro Glu Cys Pro Glu Asp Ala Phe Gln Glu Asn Gly
                485                 490                 495
Thr Pro Cys Ser Gly Gly Tyr Cys Tyr Asn Gly Ala Cys Pro Thr
                500                 505                 510
Leu Ala Gln Gln Cys Gln Ala Phe Trp Gly Pro Gly Gln Ala
                515                 520                 525
Ala Glu Glu Ser Cys Phe Ser Tyr Asp Ile Leu Pro Gly Cys Lys
                530                 535                 540
Ala Ser Arg Tyr Arg Ala Asp Met Cys Gly Val Leu Gln Cys Lys
                545                 550                 555
Gly Gly Gln Gln Pro Leu Gly Arg Ala Ile Cys Ile Val Asp Val
                560                 565                 570
Cys His Ala Leu Thr Thr Glu Asp Gly Thr Ala Tyr Glu Pro Val
                575                 580                 585
Pro Glu Gly Thr Arg Cys Gly Pro Glu Lys Val Cys Trp Lys Gly
                590                 595                 600
Arg Cys Gln Asp Leu His Val Tyr Arg Ser Ser Asn Cys Ser Ala
                605                 610                 615
Gln Cys His Asn His Gly Val Cys Asn His Lys Gln Glu Cys His
                620                 625                 630
Cys His Ala Gly Trp Ala Pro Pro His Cys Ala Lys Leu Leu Thr
                635                 640                 645
Glu Val His Ala Ala Ser Gly Ser Leu Pro Val Leu Val Val Val
                650                 655                 660
Val Leu Val Leu Leu Ala Val Val Leu Val Thr Leu Ala Gly Ile
                665                 670                 675
Ile Val Tyr Arg Lys Ala Arg Ser Arg Ile Leu Ser Arg Asn Val
                680                 685                 690
Ala Pro Lys Thr Thr Met Gly Arg Ser Asn Pro Leu Phe His Gln
                695                 700                 705
Ala Ala Ser Arg Val Pro Ala Lys Gly Gly Ala Pro Ala Pro Ser
                710                 715                 720
Arg Gly Pro Gln Glu Leu Val Pro Thr Thr His Pro Gly Gln Pro
                725                 730                 735
```

```
Ala Arg His Pro Ala Ser Ser Val Ala Leu Lys Arg Pro Pro
            740                 745                 750

Ala Pro Pro Val Thr Val Ser Ser Pro Phe Pro Val Pro Val
            755                 760                 765

Tyr Thr Arg Gln Ala Pro Lys Gln Val Ile Lys Pro Thr Phe Ala
            770                 775                 780

Pro Pro Val Pro Pro Val Lys Pro Gly Ala Gly Ala Ala Asn Pro
            785                 790                 795

Gly Pro Ala Glu Gly Ala Val Gly Pro Lys Val Ala Leu Lys Pro
            800                 805                 810

Pro Ile Gln Arg Lys Gln Gly Ala Gly Ala Pro Thr Ala Pro
            815                 820

<210> SEQ ID NO 2
<211> LENGTH: 3227
<212> TYPE: DNA
<213> ORGANISM: Homo sapien

<400> SEQUENCE: 2
```

| | |
|---|---:|
| atgcgcggcc tcgggctctg gctgctgggc gcgatgatgc tgcctgcgat | 50 |
| tgccccagc cggccctggg ccctcatgga gcagtatgag gtcgtgttgc | 100 |
| cgcggcgtct gccaggcccc cgagtccgcc gagctctgcc ctcccacttg | 150 |
| ggcctgcacc cagagagggt gagctacgtc cttggggcca cagggcacaa | 200 |
| cttcacccte cacctgcgga gaacaggga cctgctgggt tccggctaca | 250 |
| cagagaccta tacggctgcc aatggctccg aggtgacgga gcagcctcgc | 300 |
| gggcaggacc actgcttata ccagggccac gtagaggggg acccggactc | 350 |
| agccgccagc ctcagcacct gtgccggcct caggggtttc ttccaggtgg | 400 |
| ggtcagacct gcacctgatc gagccctgg atgaaggtgg cgagggcgga | 450 |
| cggcacgccg tgtaccaggc tgagcacctg ctgcagacgg ccgggacctg | 500 |
| cggggtcagc gacgacagcc tgggcagcct cctgggaccc cggacggcag | 550 |
| ccgtcttcag gcctcggccc ggggactctc tgccatcccg agagacccgc | 600 |
| tacgtggagc tgtatgtggt cgtggacaat gcagagttcc agatgctggg | 650 |
| gagcgaagca gccgtgcgtc atcgggtgct ggaggtggtg aatcacgtgg | 700 |
| acaagctata tcagaaactc aacttccgtg tggtcctggt gggcctggag | 750 |
| atttggaata gtcaggacag gttccacgtc agccccgacc ccagtgtcac | 800 |
| actggagaac ctcctgacct ggcaggcacg gcaacggaca cggcggcacc | 850 |
| tgcatgacaa cgtacagctc atcacgggtg tcgacttcac cgggactact | 900 |
| gtggggtttg ccagggtgtc cgccatgtgc tcccacagct caggggctgt | 950 |
| gaaccaggac cacagcaaga accccgtggg cgtggcctgc accatggccc | 1000 |
| atgagatggg ccacaacctg gcatggacc atgatgagaa cgtccagggc | 1050 |
| tgccgctgcc aggaacgctt cgaggccggc cgctgcatca tggcaggcag | 1100 |
| cattggctcc agtttcccca ggatgttcag tgactgcagc caggcctacc | 1150 |
| tggagagctt tttggagcgg ccgcagtcgg tgtgcctcgc caacgcccct | 1200 |
| gacctcagcc acctggtggg cggccccgtg tgtgggaacc tgtttgtgga | 1250 |
| gcgtgggag cagtgcgact gcggcccccc cgaggactgc cggaaccgct | 1300 |

```
gctgcaactc taccacctgc cagctggctg aggggggccca gtgtgcgcac        1350 ggtacctgct gccaggagtg caaggtgaag ccggctggtg agctgtgccg        1400
tcccaagaag gacatgtgtg acctcgagga gttctgtgac ggccggcacc        1450
ctgagtgccc ggaagacgcc ttccaggaga acggcacgcc ctgctccggg        1500
ggctactgct acaacggggc ctgtcccaca ctggcccagc agtgccaggc        1550
cttctggggg ccaggtgggc aggctgccga ggagtcctgc ttctcctatg        1600
acatcctacc aggctgcaag gccagccggt acagggctga catgtgtggc        1650
gttctgcagt gcaagggtgg gcagcagccc ctggggcgtg ccatctgcat        1700
cgtggatgtg tgccacgcgc tcaccacaga ggatggcact gcgtatgaac        1750
cagtgcccga gggcacccgg tgtggaccag agaaggtttg ctggaaagga        1800
cgttgccagg acttacacgt ttacagatcc agcaactgct ctgcccagtg        1850
ccacaaccat ggggtgtgca accacaagca ggagtgccac tgccacgcgg        1900
gctgggcccc gccccactgc gcgaagctgc tgactgaggt gcacgcagcg        1950
tccgggagcc tccccgtcct cgtggtggtg gttctggtgc tcctggcagt        2000
tgtgctggtc accctggcag gcatcatcgt ctaccgcaaa gcccggagcc        2050
gcatcctgag caggaacgtg gctcccaaga ccacaatggg gcgctccaac        2100
cccctgttcc accaggctgc cagccgcgtg ccggccaagg gcgggctcc        2150 agccccatcc aggggccccc aagagctggt ccccaccacc cacccgggcc        2200
agcccgcccg cacccggcc tcctcggtgg ctctgaagag gccgccccct        2250
gctcctccgg tcactgtgtc cagcccaccc ttcccagttc ctgtctacac        2300
ccggcaggca ccaaagcagg tcatcaagcc aacgttcgca cccccagtgc        2350
ccccagtcaa acccggggct ggtgcggcca accctggtcc agctgagggt        2400
gctgttggcc caaaggttgc cctgaagccc cccatccaga ggaagcaagg        2450
agccggagct cccacagcac cctagggggg cacctgcgcc tgtgtggaaa        2500
tttggagaag ttgcggcaga gaagccatgc gttccagcct tccacggtcc        2550
agctagtgcc gctcagccct agaccctgac tttgcaggct cagctgctgt        2600
tctaacctca gtaatgcatc tacctgagag gctcctgctg tccacgccct        2650
cagccaattc cttctccccg ccttggccac gtgtagcccc agctgtctgc        2700
aggcaccagg ctgggatgag ctgtgtgctt gcgggtgcgt gtgtgtgtac        2750
gtgtctccag gtggccgctg gtctcccgct gtgttcagga ggccacatat        2800
acagcccctc ccagccacac ctgcccctgc tctgggcct gctgagccgg        2850 ctgccctggg cacccggttc caggcagcac agacgtgggg catccccaga        2900
aagactccat cccaggacca ggttcccctc cgtgctcttc gagagggtgt        2950
cagtgagcag actgcacccc aagctcccga ctccaggtcc cctgatcttg        3000
ggcctgtttc ccatgggatt caagagggac agccccagct ttgtgtgtgt        3050
ttaagcttag gaatgcccct tatggaaagg gctatgtggg agagtcagct        3100
atcttgtctg gttttcttga gacctcagat gtgtgttcag cagggctgaa        3150
agcttttatt cttttaataat gagaaatgta tattttacta ataaattatt        3200
gaccgagttc tgtagattct tgttaga                                 3227
```

```
<210> SEQ ID NO 3
<211> LENGTH: 22
<212> TYPE: DNA
<213> ORGANISM: Artificial sequence
<220> FEATURE:
<223> OTHER INFORMATION: PCR primer

<400> SEQUENCE: 3
gctcagccct agaccctgac tt                                              22

<210> SEQ ID NO 4
<211> LENGTH: 32
<212> TYPE: DNA
<213> ORGANISM: Artificial sequence
<220> FEATURE:
<223> OTHER INFORMATION: PCR probe

<400> SEQUENCE: 4
caggctcagc tgctgttcta acctcagtaa tg                                   32

<210> SEQ ID NO 5
<211> LENGTH: 18
<212> TYPE: DNA
<213> ORGANISM: Artificial sequence
<220> FEATURE:
<223> OTHER INFORMATION: PCR primer

<400> SEQUENCE: 5
cgtggacagc aggagcct                                                   18

<210> SEQ ID NO 6
<211> LENGTH: 19
<212> TYPE: DNA
<213> ORGANISM: Artificial sequence
<220> FEATURE:
<223> OTHER INFORMATION: PCR primer

<400> SEQUENCE: 6
ttgctggaaa ggacgttgc                                                  19

<210> SEQ ID NO 7
<211> LENGTH: 32
<212> TYPE: DNA
<213> ORGANISM: Artificial sequence
<220> FEATURE:
<223> OTHER INFORMATION: PCR probe

<400> SEQUENCE: 7
aggacttaca cgtttacaga tccagcaact gc                                   32

<210> SEQ ID NO 8
<211> LENGTH: 19
<212> TYPE: DNA
<213> ORGANISM: Artificial sequence
<220> FEATURE:
<223> OTHER INFORMATION: PCR primer

<400> SEQUENCE: 8
gttgcacacc ccatggttg                                                  19

<210> SEQ ID NO 9
<211> LENGTH: 29
<212> TYPE: DNA
<213> ORGANISM: Artificial sequence
<220> FEATURE:
<223> OTHER INFORMATION: PCR primer
```

```
<400> SEQUENCE: 9
atgtggatcc atgcgcggcc tcgggctct                                      29

<210> SEQ ID NO 10
<211> LENGTH: 21
<212> TYPE: DNA
<213> ORGANISM: Artificial sequence
<220> FEATURE:
<223> OTHER INFORMATION: PCR primer

<400> SEQUENCE: 10
ccacagtagt cccggtgaag t                                              21

<210> SEQ ID NO 11
<211> LENGTH: 22
<212> TYPE: DNA
<213> ORGANISM: Artificial sequence
<220> FEATURE:
<223> OTHER INFORMATION: PCR primer

<400> SEQUENCE: 11
agctgactct cccacatagc cc                                             22

<210> SEQ ID NO 12
<211> LENGTH: 48
<212> TYPE: DNA
<213> ORGANISM: Artificial sequence
<220> FEATURE:
<223> OTHER INFORMATION: PCR primer

<400> SEQUENCE: 12
ggattctaat acgactcact atagggcgac tcagccgcca gcctcagc                 48

<210> SEQ ID NO 13
<211> LENGTH: 44
<212> TYPE: DNA
<213> ORGANISM: Artificial sequence
<220> FEATURE:
<223> OTHER INFORMATION: PCR primer

<400> SEQUENCE: 13
ctatgaaatt aaccctcact aaagggagcc gccgtgtccg ttgc                     44

<210> SEQ ID NO 14
<211> LENGTH: 42
<212> TYPE: DNA
<213> ORGANISM: Artificial sequence
<220> FEATURE:
<223> OTHER INFORMATION: PCR primer

<400> SEQUENCE: 14
catcaaatgc atcaagactc tctgccatcc cgagagaccc gc                       42

<210> SEQ ID NO 15
<211> LENGTH: 54
<212> TYPE: DNA
<213> ORGANISM: Artificial sequence
<220> FEATURE:
<223> OTHER INFORMATION: PCR primer

<400> SEQUENCE: 15
ccgagctcga gcggccgcag tcgattagct cccggacgct gcgtgcacct               50
cagt                                                                 54
```

<210> SEQ ID NO 16
<211> LENGTH: 17
<212> TYPE: PRT
<213> ORGANISM: Artificial sequence
<220> FEATURE:
<223> OTHER INFORMATION: Leader

<400> SEQUENCE: 16

Met Lys His Gln His Gln His Gln His Gln His Gln His Gln Met
 1               5                  10                  15

His Gln

<210> SEQ ID NO 17
<211> LENGTH: 43
<212> TYPE: DNA
<213> ORGANISM: Artificial sequence
<220> FEATURE:
<223> OTHER INFORMATION: PCR primer

<400> SEQUENCE: 17
gctgcatgaa ttcatgcgcg gcctcgggct ctggctgctg ggc                    43

<210> SEQ ID NO 18
<211> LENGTH: 46
<212> TYPE: DNA
<213> ORGANISM: Artificial sequence
<220> FEATURE:
<223> OTHER INFORMATION: PCR primer

<400> SEQUENCE: 18
gagttttgtc ggtgaccgac ccggacgctg cgtgcacctc agtcag                 46

<210> SEQ ID NO 19
<211> LENGTH: 10
<212> TYPE: PRT
<213> ORGANISM: Homo sapien

<400> SEQUENCE: 19

Met Arg Gly Leu Gly Leu Trp Leu Leu Gly
 1               5                  10

<210> SEQ ID NO 20
<211> LENGTH: 10
<212> TYPE: PRT
<213> ORGANISM: Homo sapien

<400> SEQUENCE: 20

Leu Thr Glu Val His Ala Ala Ser Gly Ser
 1               5                  10

<210> SEQ ID NO 21
<211> LENGTH: 9
<212> TYPE: PRT
<213> ORGANISM: Homo sapien

<400> SEQUENCE: 21

Asp Ser Leu Pro Ser Arg Glu Thr Arg
 1               5

<210> SEQ ID NO 22
<211> LENGTH: 9

```
<212> TYPE: PRT
<213> ORGANISM: Homo sapien

<400> SEQUENCE: 22

Thr Glu Val His Ala Ala Ser Gly Ser
 1               5
```

COMPOSITIONS AND METHODS FOR THE TREATMENT OF TUMORS

This application is a continuation of application Ser. No. 09/627,202, filed Jul. 27, 2000, now abandoned, which claims the benefit of application Ser. No. 60/146,217, filed Jul. 28, 1999 under 35 U.S.C. §119(e), which applications are incorporated herein by reference.

FIELD OF THE INVENTION

The present invention relates to compositions and methods for the diagnosis and treatment of tumors.

BACKGROUND OF THE INVENTION

Malignant tumors (cancers) are the second leading cause of death in the United States, after heart disease (Boring et al., *CA Cancel J. Clin.* 43:7 [993]).

Cancer is characterized by an increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state, a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers. The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype (Hunter, *Cell* 64:1129 [1991] and Bishop, *Cell* 64:235–248 [1991]).

A well known mechanism of gene (e.g. oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome (Alitalo et al., *Adv. Cancer Res.* 47:235–281 [1986]). It is believed that the overexpression of the gene parallels gene amplification, i.e. is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor (p185$^{HER2}$; HER2) related to the epidermal growth factor receptor EGFR), is overexpressed in about 25% to 30% of human breast cancer (Slamon et al., *Science* 235: 177–182 [1987]; Slamon et al., *Science* 244:707–712 [1989]).

It has been reported that gene amplification of a proto-oncogene is an event typically involved in the more malignant forms of cancer, and could act as a predictor of clinical outcome (Schwab et al., *Genes Chromosomes Cancer* 1:181–193 [1990]; Alitalo et al., supra). Thus, erbB2 overexpression is commonly regarded as a predictor of a poor prognosis, especially in patients with primary disease that involves axillary lymph nodes (Slamon et al., [1987] and [1989], supra; Ravdin and Chamness, *Gene* 159:19–27 [1995]; and Hynes and Stern, *Biochim Biophys Acta* 1198: 165–184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11 (3 Suppl 1):43–48 [1997]). However, despite the association of erbB2 overexpression with poor prognosis, the odds of HER2-positive patients responding clinically to treatment with taxanes were greater than three times those of HER2-negative patients (Ibid). A recombinant humanized anti-ErbB2 (anti-HER2) monoclonal antibody (a humanized version of the murine anti-ErbB2 antibody 4D5, referred to as rhuMAb HER2 or Herceptin™) has been clinically active in patients with ErbB2-overexpressing metastatic breast cancers that had received extensive prior anticancer therapy. (Baselga et al., *J. Clin. Oncol.* 14:737–744 [1996]).

Murine ADAM8 (also known as MS2 and mCD156) was initially cloned from macrophages and macrophage cell lines and described as a cell surface antigen. (Yoshida, S., et al (1990) *Intl Immunology* 2:585–591). Although not initially recognized, mADAM8 has a structure resembling the metalloproteinase domain of hemorahagic snake venom proteins on the amino-terminal side of a cysteine-rich region and may play a role in tissue infiltration of myelomonocytic cells. (Higuchi, Y. et al (1996) *Tissue Antigens* 48:423; Kataoka, M. et al (1997) *J. Biol Chem* 29:18209–18215) Human ADAM8 (hADAM8, also known as hCD156) has been cloned and the corresponding gene mapped to chromosome 10q26.3. hADAM8 exhibits 61.7% homology with mADAM8 and displays disintegrin and metalloproteinase domains. (Yoshiyama, K. et al (1997) *Genomics* 41:56–62). It has also been reported that an ADAM8 peptide enhanced tolerance induction in a rat model of generalized autoimmunity of the nervous system. (Schluesener, H. (1998) *J Neuroimmunology* 87:197–202).

WO 9740072 describes ADAM12 proteins and uses thereof.

In light of the above, there is obvious interest in identifying novel methods and compositions which are useful for diagnosing and treating tumors which are associated with gene amplification.

SUMMARY OF THE INVENTION

The present invention concerns compositions and methods for the diagnosis and treatment of neoplastic cell growth and proliferation in mammals, including humans. The present invention is based on the identification of a gene that is amplified in the genome of tumor cells. Such gene amplification is associated with the overexpression of the gene product and contributes to tumorigenesis. Accordingly, the proteins encoded by the amplified genes are useful targets for the diagnosis and/or treatment (including prevention) of certain cancers, and act as predictors of the prognosis of tumor treatment.

Although not initially recognized by those who cloned the murine molecule, ADAM8 contains a metalloprotease and a disintegrin domain. It was also isolated as an antigen present on monocytes. Thus, ADAM8 is believed to play a role in the migration of monocytes through the extracellular matrix or perhaps in the processing of cytokines or other chemotactic molecules. Increased ADAM8 expression on tumor cells, in stroma adjacent to tumor cells or in epithelial cells, for example, provides a means by which tumor cells can migrate through the extracellular matrix or process cytokines or other chemotactic molecules. Increased ADAM8 expression in or near tumor cells, therefore, provides a means by which tumor cells invade tissue or form metastases. Targeting such a molecule with an antibody or another molecule that blocks, inactivates or otherwise incapacitates the ability of tumor cells to move into or out of tissue results in a clinically relevant anti-tumor therapeutic.

In one embodiment, the present invention concerns an isolated antibody that binds to a polypeptide designated herein as ADAM8. In one aspect, the isolated antibody specifically binds to an ADAM8 polypeptide. In another aspect, the antibody induces the death of a cell that expresses an ADAM8 polypeptide. Often, the cell that expresses the ADAM8 polypeptide is a tumor cell that overexpresses the polypeptide as compared to a normal cell of the same type. In yet another aspect, the antibody is a monoclonal antibody, which preferably has non-human complementarity determining region (CDR) residues and human framework region (FR) residues. The antibody may be labeled and may be immobilized on a solid support. In yet another aspect, the antibody is an antibody fragment, a single-chain antibody, or an anti-idiotypic antibody that binds, preferably specifically, to an ADAM8 polypeptide.

In another embodiment, the invention concerns a composition of matter that comprises an antibody that binds, preferably specifically, to an ADAM8 polypeptide in admixture with a pharmaceutically acceptable carrier. In one aspect, the composition of matter comprises a therapeutically effective amount of the antibody. In another aspect, the composition comprises a further active ingredient, which may, for example, be a further antibody or a cytotoxic or chemotherapeutic agent. Preferably, the composition is sterile.

In a further embodiment, the invention concerns an isolated nucleic acid molecule that encodes an anti-ADAM8 antibody, and vectors and recombinant host cells comprising such nucleic acid molecules.

In a still further embodiment, the invention concerns a method for producing an anti-ADAM8 antibody, wherein the method comprises culturing a host cell transformed with a nucleic acid molecule which encodes the antibody under conditions sufficient to allow expression of the antibody, and recovering the antibody from the cell culture.

The invention further concerns antagonists of an ADAM8 polypeptide that inhibit one or more of the functions or activities of an ADAM8 polypeptide. Agonists of an ADAM8 polypeptide are also contemplated herein.

In a further embodiment, the invention concerns an isolated nucleic acid molecule that hybridizes to the complement of a nucleic acid molecule encoding an ADAM8 polypeptide. The isolated nucleic acid molecule is preferably DNA, and hybridization preferably occurs under stringent hybridization and wash conditions. Such nucleic acid molecules can act as antisense molecules of the amplified genes identified herein, which, in turn, can find use in the modulation of the respective amplified genes, or as antisense primers in amplification reactions. Furthermore, such sequences can be used as part of a ribozyme and/or a triple helix sequence which, in turn, may be used in regulation of the amplified genes.

In another embodiment, the invention provides a method for determining the presence of an ADAM8 polypeptide in a sample suspected of containing an ADAM8 polypeptide, wherein the method comprises exposing the sample to an anti-ADAM8 antibody and determining binding of the antibody to an ADAM8 polypeptide in the sample. In another embodiment, the invention provides a method for determining the presence of an ADAM8 polypeptide in a cell, wherein the method comprises exposing the cell to an anti-ADAM8 antibody and determining binding of the antibody to the cell.

In yet another embodiment, the present invention concerns a method of diagnosing tumor in a mammal, comprising detecting the level of expression of a gene encoding an ADAM8 polypeptide (a) in a test sample of tissue cells obtained from the mammal, and (b) in a control sample of known normal tissue cells of the same cell type, wherein a higher expression level in the test sample is indicative of the presence of tumor in the mammal from which the test tissue cells were obtained.

In another embodiment, the present invention concerns a method of diagnosing tumor in a mammal, comprising (a) contacting an anti-ADAM8 antibody with a test sample of tissue cells obtained from the mammal, and (b) detecting the formation of a complex between the anti-ADAM8 antibody and an ADAM8 polypeptide in the test sample, wherein the formation of a complex is indicative of the presence of a tumor in said mammal. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art.

The test sample is usually obtained from an individual suspected to have neoplastic cell growth or proliferation (e.g. cancerous cells).

In another embodiment, the present invention concerns a cancer diagnostic kit comprising an anti-ADAM8 antibody and a carrier (e.g. a buffer) in suitable packaging. The kit preferably contains instructions for using the antibody to detect the presence of an ADAM8 polypeptide in a sample suspected of containing the same.

In yet another embodiment, the invention concerns a method for inhibiting the growth of tumor cells comprising exposing tumor cells which express an ADAM8 polypeptide to an effective amount of an agent which inhibits an activity and/or the expression of an ADAM8 polypeptide, wherein growth of the tumor cells is thereby inhibited. The agent preferably is an anti-ADAM8 antibody, a small organic and inorganic molecule, peptide, phosphopeptide, antisense or ribozyme molecule, or a triple helix molecule. In a specific aspect, the agent, e.g. the anti-ADAM8 antibody, induces cell death. In a further aspect, the tumor cells are further exposed to radiation treatment and/or a cytotoxic or chemotherapeutic agent.

In a further embodiment, the invention concerns an article of manufacture, comprising:

a container;

a label on the container; and a composition comprising an active agent contained within the container; wherein the composition is effective for inhibiting the growth of tumor cells and the label on the container indicates that the composition can be used for treating conditions characterized by overexpression of an ADAM8 polypeptide as compared to a normal cell of the same tissue type. In particular aspects, the active agent in the composition is an agent which inhibits an activity and/or the expression of an ADAM8 polypeptide. In preferred aspects, the active agent is an anti-ADAM8 antibody or an antisense oligonucleotide.

The invention also provides a method for identifying a compound that inhibits an activity of an ADAM8 polypeptide, comprising contacting a candidate compound with an ADAM8 polypeptide under conditions and for a time sufficient to allow these two components to interact and determining whether an activity of the ADAM8 polypeptide is inhibited. In a specific aspect, either the candidate compound or the ADAM8 polypeptide is immobilized on a solid support. In another aspect, the non-immobilized component carries a detectable label. In a preferred aspect, this method comprises the steps of (a) contacting cells and a candidate compound to be screened in the presence of ADAM8 polypeptide under conditions suitable for the induction of a cellular response normally induced by an ADAM8 polypeptide and (b) determining the induction of said cellular response to determine if the test compound is an effective antagonist.

In another embodiment, the invention provides a method for identifying a compound that inhibits the expression of an ADAM8 polypeptide in cells that express the polypeptide, wherein the method comprises contacting the cells with a candidate compound and determining whether the expression of the ADAM8 polypeptide is inhibited. In a preferred aspect, this method comprises the steps of (a) contacting cells and a candidate compound to be screened under conditions suitable for allowing expression of the ADAM8 polypeptide and (b) determining the inhibition of expression of said polypeptide.

ADAM8 Sequences

An amino acid sequence of native ADAM8 protein is shown below:

(SEQ ID NO:1)
MRGLGLWLLGAMMLPAIAPSRPWALMEQYEVVLPRRLPGPRVRRALPSHL

GLHPERVSYVLGATGHNFTLHLRKNRDLLGSGYTETYTAANGSEVTEQPR

GQDHCLYQGHVEGYPDSAASLSTCAGLRGFFQVGSDLHLIEPLDEGGEGG

RHAVYQAEHLLQTAGTCGVSDDSLGSLLGPRTAAVFRPRPGDSLPSRETR

YVELYVVVDNAEFQMLGSEAAVRHRVLEVVNHVDKLYQKLNFRVVLVGLE

IWNSQDRFHVSPDPSVTLENLLTWQARQRTRRHLHDNVQLITGVDFTGTT

VGFARVSAMCSHSSGAVNQDHSKNPVGVACTMAHEMGHNLGMDHDENVQG

CRCQERFEAGRCIMAGSIGSSFPRMFSDCSQAYLESFLERPQSVCLANAP

DLSHLVGGPVCGNLFVERGEQCDCGPPEDCRNRCCNSTTCQLAEGAQCAH

GTCCQECKVKPAGELCRPKKDMCDLEEFCDGRHPECPEDAFQENGTPCSG

GYCYNGACPTLAQQCQAFWGPGGQAAEESCFSYDILPGCKASRYRADMCG

VLQCKGGQQPLGRAICIVDVCHALTTEDGTAYEPVPEGTRCGPEKVCWKG

RCQDLHVYRSSNCSAQCHNHGVCNHKQECHCHAGWAPPHCAKLLTEVHAA

SGSLPVLVVVVLVLLAVVLVTLAGIIVYRKARSRILSRNVAPKTTMGRSN

PLFHQAASRVPAKGGAPAPSRGPQELVPTTHPGQPARHPASSVALKRPPP

APPVTVSSPPFPVPVYTRQAPKQVIKPTFAPPVPPVKPGAGAANPGPAEG

AVGPKVALKPPIQRKQGAGAPTAP

A DNA sequence encoding the ADAM8 amino acid polypeptide shown above is shown below:

(SEQ ID NO:2)
ATGCGCGGCCTCGGGCTCTGGCTGCTGGGCGCGATGATGCTGCCTGCGAT

TGCCCCCAGCCGGCCCTGGGCCCTCATGGAGCAGTATGAGGTCGTGTTGC

CGCGGCGTCTGCCAGGCCCCCGAGTCCGCCGAGCTCTGCCCTCCCACTTG

GGCCTGCACCCAGAGAGGGTGAGCTACGTCCTTGGGGCCACAGGGCACAA

CTTCACCCTCCACCTGCGGAAGAACAGGGACCTGCTGGGTTCCGGCTACA

CAGAGACCTATACGGCTGCCAATGGCTCCGAGGTGACGGAGCAGCCTCGC

GGGCAGGACCACTGCTTATACCAGGGCCACGTAGAGGGGTACCCGGACTC

AGCCGCCAGCCTCAGCACCTGTGCCGGCCTCAGGGGTTTCTTCCAGGTGG

GGTCAGACCTGCACCTGATCGAGCCCCTGGATGAAGGTGGCGAGGGCGGA

CGGCACGCCGTGTACCAGGCTGAGCACCTGCTGCAGACGGCCGGGACCTG

CGGGGTCAGCGACGACAGCCTGGGCAGCCTCCTGGGACCCCGGACGGCAG

CCGTCTTCAGGCCTCGGCCCGGGGACTCTCTGCCATCCCGAGAGACCCGC

TACGTGGAGCTGTATGTGGTCGTGGACAATGCAGAGTTCCAGATGCTGGG

GAGCGAAGCAGCCGTGCGTCATCGGGTGCTGGAGGTGGTGAATCACGTGG

ACAAGCTATATCAGAAACTCAACTTCCGTGTGGTCCTGGTGGGCCTGGAG

ATTGGAATAGTCAGGACAGGTTCCACGTCAGCCCCGACCCCAGTGTCACA

CTGGAGAACCTCCTGACCTGGCAGGCACGGCAACGGACACGGCGGCACCT

GCATGACAACGTACAGCTCATCACGGGTGTCGACTTCACCGGGACTACTG

TGGGGTTTGCCAGGGTGTCCGCCATGTGCTCCCACAGCTCAGGGGCTGTG

AACCAGGACCACAGCAAGAACCCCGTGGGCGTGGCCTGCACCATGGCCCA

TGAGATGGGCCACAACCTGGGCATGGACCATGATGAGAACGTCCAGGGCT

GCCGCTGCCAGGAACGCTTCGAGGCCGGCCGCTGCATCATGGCAGGCAGC

ATTGGCTCCAGTTTCCCCAGGATGTTCAGTGACTGCAGCCAGGCCTACCT

GGAGAGCTTTTTGGAGCGGCCGCAGTCGGTGTGCCTCGCCAACGCCCCTG

ACCTCAGCCACCTGGTGGGCGGCCCCGTGTGTGGGAACCTGTTTGTGGAG

CGTGGGGAGCAGTGCGACTGCGGCCCCCCCGAGGACTGCCGGAACCGCTG

CTGCAACTCTACCACCTGCCAGCTGGCTGAGGGGCCCAGTGTGCGCACG

GTACCTGCTGCCAGGAGTGCAAGGTGAAGCCGGCTGGTGAGCTGTGCCGT

CCCAAGAAGGACATGTGTGACCTCGAGGAGTTCTGTGACGGCCGGCACCC

TGAGTGCCCGGAAGACGCCTTCCAGGAGAACGGCACGCCCTGCTCCGGGG

GCTACTGCTACAACGGGGCCTGTCCCACACTGGCCCAGCAGTGCCAGGCC

TTCTGGGGGCCAGGTGGGCAGGCTGCCGAGGAGTCCTGCTTCTCCTATGA

CATCCTACCAGGCTGCAAGGCCAGCCGGTACAGGGCTGACATGTGTGGCG

TTCTGCAGTGCAAGGGTGGGCAGCAGCCCCTGGGGCGTGCCATCTGCATC

GTGGATGTGTGCCACGCGCTCACCACAGAGGATGGCACTGCGTATGAACC

AGTGCCCGAGGGCACCCGGTGTGGACCAGAGAAGGTTTGCTGGAAAGGAC

-continued

```
GTTGCCAGGACTTACACGTTTACAGATCCAGCAACTGCTCTGCCCAGTGC

CACAACCATGGGGTGTGCAACCACAAGCAGGAGTGCCACTGCCACGCGGG

CTGGGCCCCGCCCCACTGCGCGAAGCTGCTGACTGAGGTGCACGCAGCGT

CCGGGAGCCTCCCCGTCCTCGTGGTGGTGGTTCTGGTGCTCCTGGCAGTT

GTGCTGGTCACCCTGGCAGGCATCATCGTCTACCGCAAAGCCCGGAGCCG

CATCCTGAGCAGGAACGTGGCTCCCAAGACCACAATGGGCGCTCCAACC

CCCTGTTCCACCAGGCTGCCAGCCGCGTGCCGGCCAAGGGCGGGGCTCCA

GCCCCATCCAGGGGCCCCCAAGAGCTGGTCCCCACCACCCACCCGGGCCA

GCCCGCCCGACACCCGGCCTCCTCGGTGGCTCTGAAGAGGCCGCCCCCTG

CTCCTCCGGTCACTGTGTCCAGCCCACCCTTCCCAGTTCCTGTCTACACC

CGGCAGGCACCAAAGCAGGTCATCAAGCCAACGTTCGCACCCCCAGTGCC

CCCAGTCAAACCCGGGGCTGGTGCGGCCAACCCTGGTCCAGCTGAGGGTG

CTGTTGGCCCAAAGGTTGCCCTGAAGCCCCCATCCAGAGGAAGCAAGGA

GCCGGAGCTCCCACAGCACCCTAGGGGGGCACCTGCGCCTGTGTGGAAAT

TTGGAGAAGTTGCGGCAGAGAAGCCATGCGTTCCAGCCTTCCACGGTCCA

GCTAGTGCCGCTCAGCCCTAGACCCTGACTTTGCAGGCTCAGCTGCTGTT

CTAACCTCAGTAATGCATCTACCTGAGAGGCTCCTGCTGTCCACGCCCTC

AGCCAATTCCTTCTCCCCGCCTTGGCCACGTGTAGCCCCAGCTGTCTGCA

GGCACCAGGCTGGGATGAGCTGTGTGCTTGCGGGTGCGTGTGTGTACG

TGTCTCCAGGTGGCCGCTGGTCTCCCGCTGTGTTCAGGAGGCCACATATA

CAGCCCCTCCCAGCCACACCTGCCCCTGCTCTGGGGCCTGCTGAGCCGGC

TGCCCTGGGCACCCGGTTCCAGGCAGCACAGACGTGGGGCATCCCCAGAA

AGACTCCATCCCAGGACCAGGTTCCCCTCCGTGCTCTTCGAGAGGGTGTC

AGTGAGCAGACTGCACCCCAAGCTCCCGACTCCAGGTCCCCTGATCTTGG

GCCTGTTTCCCATGGGATTCAAGAGGGACAGCCCCAGCTTTGTGTGTGTT

TAAGCTTAGGAATGCCCTTTATGGAAAGGGCTATGTGGGAGAGTCAGCTA

TCTTGTCTGGTTTTCTTGAGACCTCAGATGTGTGTTCAGCAGGGCTGAAA

GCTTTTATTCTTTAATAATGAGAAATGTATATTTTACTAATAAATTATTG

ACCGAGTTCTGTAGATTCTTGTTAGA
```

See Yoshida S., et al. (1990) Intl Immunology 2(6):585–91 and Yoshiyama, K. et al (1997) Genomics 41:56-62.

Description of Tables 1 and 2

Tables 1A–D show hypothetical exemplifications for using the below described method to determine % amino acid sequence identity (Tables 1A–B) and % nucleic acid sequence identity (Tables 1C–D) using the ALIGN-2 sequence comparison computer program, wherein "PRO" represents the amino acid sequence of a hypothetical ADAM8 polypeptide of interest, "Comparison Protein" represents the amino acid sequence of a polypeptide against which the "PRO" polypeptide of interest is being compared, "PRO-DNA" represents a hypothetical ADAM8-encoding nucleic acid sequence of interest, "Comparison DNA" represents the nucleotide sequence of a nucleic acid molecule against which the "PRO-DNA" nucleic acid molecule of interest is being compared, "X," "Y" and "Z" each represent different hypothetical amino acid residues and "N", "L" and "V" each represent different hypothetical nucleotides.

Tables 2A–Q provide the complete source code for the ALIGN-2 sequence comparison computer program. This source code may be routinely compiled for use on a UNIX operating system to provide the ALIGN-2 sequence comparison computer program.

DETAILED DESCRIPTION OF THE INVENTION

I. Definitions

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e. the level of gene expression, also increases in the proportion of the number of copies made of the particular gene expressed.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Mammal" for purposes of treatment refers to any animal classified as a mammal, including humans, domestic and farm animals, and zoo, sports, or pet animals, such as dogs, horses, cats, cattle, pigs, sheep, etc. Preferably, the mammal is human.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids;

antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol®, Bristol-Myers Squibb Oncology, Princeton, N.J.), and doxetaxel (Taxotere®, Rhone-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675, 187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), Taxol®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13.

"Doxorubicin" is an athracycline antibiotic. The full chemical name of doxorubicin is (8S-cis)-10-[(3-amino-2, 3,6-trideoxy-alpha-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha , -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11 IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g. Wilman, "Prodrugs in Cancer Chemotherapy", *Biochemical Society Transactions,* 14:375–382, 615th Meeting, Belfast (1986), and Stella et al., "Prodrugs: A Chemical Approach to Targeted Drug Delivery", Directed Drug Delivery, Borchardt et al., (ed.), pp. 147–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glysocylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrugs form for use in this invention include, but are not limited to, those chemotherapeutic agents described above.

The terms "ADAM8" or "ADAM8 polypeptide" when used herein encompass native sequence ADAM8 polypeptides and ADAM8 polypeptide variants (which are further defined herein) and are preferably human polypeptides. The ADAM8 polypeptide may be isolated from a variety of sources, such as from human tissue types or from another source, or prepared by recombinant and/or synthetic methods.

A "native sequence" ADAM8 polypeptide comprises a polypeptide having the same amino acid sequence as an ADAM8 polypeptide derived from nature. Such native sequence ADAM8 polypeptide can be isolated from nature or can be produced by recombinant and/or synthetic means. The term "native sequence" ADAM8 polypeptide specifically encompasses naturally-occurring truncated or secreted forms (e.g., an extracellular domain sequence), naturally-occurring variant forms (e.g., alternatively spliced forms) and naturally-occurring allelic variants of the ADAM8 polypeptide. In certain embodiments of the invention, the native sequence ADAM8 polypeptide is a mature or full-length native sequence ADAM8 polypeptide comprising the amino acid sequence shown above (SEQ ID NO: 1). Fragments of the respective native polypeptides herein include, but are not limited, to polypeptide variants from which the native N-terminal signal sequence has been fully or partially deleted or replaced by another sequence, and extracellular domains of the respective native sequences, regardless whether such truncated (secreted) forms occur in nature. Fragments are preferably sufficient in length for the production of an antibody specifically binding the corresponding native "ADAM8" polypeptide.

"ADAM8 variant polypeptide" means an active ADAM8 polypeptide as defined below having at least about 80% amino acid sequence identity with the amino acid sequence shown above (SEQ ID NO: 1), or a specifically derived fragment thereof. Such ADAM8 variant polypeptides include, for instance, ADAM8 polypeptides wherein one or more amino acid residues are added, or deleted, at the N- and/or C-terminus, as well as within one or more internal domains, of the sequence of SEQ ID NO: 1, respectively. Ordinarily, an ADAM8 variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with the amino acid sequence of SEQ ID NO: 1, respectively, or a derived polypeptide fragment thereof. Variants do not encompass the native ADAM8 polypeptide sequence.

"Percent (%) amino acid sequence identity" with respect to the ADAM8 polypeptide sequences identified herein is defined as the percentage of amino acid residues in a candidate sequence that are identical with the amino acid residues in the ADAM8 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. The % amino acid sequence identity values used herein are generated using the WU-BLAST-2 computer program [Altschul et al., *Methods in Enzymology*, 266:460–480 (1996)]. WU-BLAST-2 uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between the ADAM8 polypeptide amino acid sequence and the comparison amino acid sequence of interest (i.e., the sequence against which the ADAM8 polypeptide is being compared) as determined by WU-BLAST-2 by (b) the total number of amino acid residues of the ADAM8 polypeptide of interest.

Notwithstanding the above, % amino acid sequence identity values may also be determined using the computer program ALIGN-2 which was authored by Genentech, Inc. and which has been filed with user documentation in the U.S. Copyright Office, Washington D.C., 20559 and which is registered under U.S. Copyright Registration No. TXU510087. All search parameters are set by the ALIGN-2 program and do not vary. See Tables 2A–Q.

"ADAM8 variant polynucleotide" or "ADAM8 variant nucleic acid sequence" means an active ADAM8 polypeptide-encoding nucleic acid molecule as defined below having at least about 80% nucleic acid sequence identity with the nucleotide acid sequence shown above (SEQ ID NO: 2) or a specifically derived fragment thereof. Ordinarily, an ADAM8 variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with the nucleic acid sequence of SEQ ID NO: 2 or a derived fragment thereof. Variants do not encompass the native nucleotide sequence. In this regard, due to the degeneracy of the genetic code, one of ordinary skill in the art will immediately recognize that a large number of ADAM8 variant polynucleotides having at least about 80% nucleic acid sequence identity to the nucleotide sequence of SEQ ID NO: 2 will encode a polypeptide having an amino acid sequence which is identical to the amino acid sequence of SEQ ID NO: 1.

"Percent (%) nucleic acid sequence identity" with respect to the ADAM8 polypeptide-encoding nucleic acid sequences identified herein is defined as the percentage of nucleotides in a candidate sequence that are identical with the nucleotides in the ADAM8 polypeptide-encoding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. The % identity values used herein are generated using the WU-BLAST-2 computer program [Altschul et al., supra]. WU-BLAST-2 uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % nucleic acid sequence identity value is determined by dividing (a) the number of matching identical nucleotides between the ADAM8 polypeptide-encoding nucleic acid sequence and the comparison nucleic acid sequence of interest (i.e., the sequence against which the ADAM8 polypeptide-encoding nucleic acid sequence is being compared) as determined by WU-BLAST-2 by (b) the total number of nucleotides of the ADAM8 polypeptide-encoding nucleic acid of interest.

Notwithstanding the above, % nucleic acid sequence identity values may also be determined using the computer program ALIGN-2 which was authored by Genentech, Inc. and which has been filed with user documentation in the U.S. Copyright Office, Washington D.C., 20559 and which is registered under U.S. Copyright Registration No. TXU510087. All search parameters are set by the ALIGN-2 program and do not vary. See Tables 2A–Q In other embodiments, ADAM8 variant polynucleotides are nucleic acid molecules that encode an active ADAM8 polypeptide and which are capable of hybridizing, preferably under stringent hybridization and wash conditions, to nucleotide sequences encoding the full-length ADAM8 polypeptide (SEQ ID NO: 1). ADAM8 variant polypeptides may be those that are encoded by an ADAM8 variant polynucleotide.

The term "positives", in the context of the amino acid sequence identity comparisons performed as described above, includes amino acid residues in the sequences compared that are not identical but have similar properties (e.g., as a result of conservative substitutions; see Table 3 below). The % value of positives is determined by dividing (a) the number of amino acid residues scoring a positive value in the BLOSUM62 matrix between the ADAM8 polypeptide amino acid sequence and the comparison amino acid sequence of interest (i.e., the amino acid sequence against which the ADAM8 polypeptide sequence is being compared) as determined by WU-BLAST-2 by (b) the total number of amino acid residues of the ADAM8 polypeptide of interest. See Tables 1A–D.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the ADAM8 natural environment will not be present. Ordinarily, however, isolated polypeptide will be prepared by at least one purification step.

An "isolated" nucleic acid molecule encoding a ADAM8 polypeptide is a nucleic acid molecule that is identified and separated from at least one contaminant nucleic acid molecule with which it is ordinarily associated in the natural source of ADAM8-encoding nucleic acid. An isolated ADAM8-encoding nucleic acid molecule is other than in the form or setting in which it is found in nature. Isolated nucleic acid molecules therefore are distinguished from the ADAM8-encoding nucleic acid molecule as it exists in natural cells. However, an isolated nucleic acid molecule encoding an ADAM8 polypeptide includes nucleic acid molecules contained in cells that ordinarily express ADAM8 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual,* New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 35–50° C. The skilled artisan will recognize how to adjust the temperature, ionic strength, etc. as necessary to accommodate factors such as probe length and the like.

The term "epitope tagged" when used herein refers to a chimeric polypeptide comprising an ADAM8 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of molecules identified based upon the ADAM8 polypeptides (or their coding sequences) refers to polypeptides (e.g. antibodies) or organic or inorganic small molecules, peptides, etc. which retain a biological and/or an immunological activity/property of a native or naturally-occurring ADAM8 polypeptide.

"Biological activity" in the context of an antibody or another molecule that can be identified by the screening assays disclosed herein (e.g. an organic or inorganic small molecule, peptide, etc.) is used to refer to the ability of such molecules to bind or complex with the polypeptides encoded by the amplified genes identified herein, or otherwise interfere with the interaction of the encoded polypeptides with other cellular proteins. A preferred biological activity is growth inhibition of a target tumor cell. Another preferred biological activity is cytotoxic activity resulting in the death of the target tumor cell.

The phrase "immunological property" means immunological cross-reactivity with at least one epitope of an ADAM8 polypeptide.

"Immunological cross-reactivity" as used herein means that the candidate polypeptide is capable of competitively inhibiting the qualitative biological activity of an ADAM8 polypeptide having this activity with polyclonal antisera raised against the known active ADAM8 polypeptide. Such antisera are prepared in conventional fashion by injecting goats or rabbits, for example, subcutaneously with the known active analogue in complete Freund's adjuvant, followed by booster intraperitoneal or subcutaneous injection in incomplete Freunds. The immunological cross-reactivity preferably is "specific", which means that the binding affinity of the immunologically cross-reactive molecule (e.g. antibody) identified, to the corresponding ADAM8 polypeptide is significantly higher (preferably at least about 2-times, more preferably at least about 4-times, even more preferably at least about 8-times, most preferably at least about 8-times higher) than the binding affinity of that molecule to any other known native polypeptide.

The term "antagonist" is used in the broadest sense, and includes any molecule that partially or fully blocks, inhibits, or neutralizes a biological activity of a native ADAM8 polypeptide disclosed herein. In a similar manner, the term "agonist" is used in the broadest sense and includes any molecule that mimics a biological activity of a native ADAM8 polypeptide disclosed herein. Suitable agonist or antagonist molecules specifically include agonist or antagonist antibodies or antibody fragments, fragments or amino acid sequence variants of native polypeptides, peptides, small organic molecules, etc.

A "small molecule" is defined herein to have a molecular weight below about 500 Daltons.

"Antibodies" (Abs) and "immunoglobulin" (Igs) are glycoproteins having the same structural characteristics. While antibodies exhibit binding specificity to a specific antigen, immunoglobulin include both antibodies and other antibody-like molecules that lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g., bispecific antibodies) formed from at least two intact antibodies, and antibody fragments so long as they exhibit the desired biological activity.

"Native antibodies" and "native immunoglobulin" are usually heterotetrameric glycoproteins of about 150,000 Dalton, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta—sheet configuration, connected by three CDRs, which form loops connecting, and in some cases forming part of, the—sheet structure. The CDRs in each chain are held together in close proximity with the FR regions and, with the CDRs from the other chain, contribute to the formation of the antigen-binding site of antibodies (see Kabat et al., *NIH Publ. No.*91-3242, Vol. I, pages 647–669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" to "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest,* 5th Ed. Public Health Service, National Institute of Health, Bethesda, Md. [1991]) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Clothia and Lesk, *J. Mol. Biol.* 196:901–917 [1987]). "Framework" or "FR" residues are those variable domain residues other than the hypervariable region residues as herein defined.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulin) from any vertebrate species can be assigned to one of two clearly distinct types, called kappa and lambda, based on the amino acid sequences of their constant domains.

Depending on the amino acid sequence of the constant domain of their heavy chains, immunoglobulin can be assigned to different classes. There are five major classes of immunoglobulin: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulin are called alpha, delta, epsilon, gamma, and μ, respectively. The subunit structures and three-dimensional configurations of different classes of immunoglobulin are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 [1975], or may be made by recombinant DNA methods (see, e.g., U.S. Pat. No. 4,816,567). The "monoclonal antibodies" may also be isolated from phage antibody libraries using the techniques described in Clackson et al., *Nature,* 352:624–628 [1991] and Marks et al., *J. Mol. Biol.,* 222:581–597 (1991), for example.

The monoclonal antibodies herein specifically include "chimeric" antibodies (immunoglobulin) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851–6855 [1984]).

"Humanized" forms of non-human (e.g., murine) antibodies are chimeric immunoglobulin, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulin (recipient antibody) in which residues from a CDR of the recipient are replaced by residues from a CDR of a non-human species (donor antibody) such as mouse, rat or rabbit having the desired specificity, affinity, and capacity. In some instances, corresponding non-human residues replace Fv FR residues of the human immunoglobulin. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature 321:522–525 (1986); Reichmann et al., Nature 332:323–329 [1988]; and Presta; Curr. Op. Struct. Biol. 2:593–596 (1992). The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition which is detectable. Radionuclides that can serve as detectable labels include, for example, I-131, I-123, I-125, Y-90, Re-188, Re-186, At-211, Cu-67, Bi-212, and Pd-109.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an ADAM8 polypeptide or antibody thereto and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

II. Compositions and Methods of the Invention

A. Full-length ADAM8 Polypeptide

The present invention provides newly identified and isolated nucleotide sequences encoding polypeptides referred to in the present application as ADAM8. In particular, cDNA encoding ADAM8 polypeptides has been identified and isolated, as disclosed in further detail in the Examples below. In the present specification the proteins encoded by the herein disclosed nucleic acid sequences as well as all further native homologues and variants included in the foregoing definition of ADAM8, will be referred to as "ADAM8", regardless of their origin or mode of preparation.

B. ADAM8 Variants

In addition to the full-length native sequence ADAM8 polypeptides described herein, it is contemplated that ADAM8 variants can be prepared. ADAM8 variants can be prepared by introducing appropriate nucleotide changes into the ADAM8 DNA, and/or by synthesis of the desired ADAM8 polypeptide. Those skilled in the art will appreciate that amino acid changes may alter post-translational processes of the ADAM8, such as changing the number or position of glycosylation sites or altering the membrane anchoring characteristics.

Variations in the native full-length sequence ADAM8 or in various domains of the ADAM8 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the ADAM8 that results in a change in the amino acid sequence of the ADAM8 as compared with the native sequence ADAM8. Optionally the variation is by substitution of at least one amino acid with any other amino acid in one or more of the domains of the ADAM8. Guidance in determining which amino acid residue may be inserted, substituted or deleted without adversely affecting the desired activity may be found by comparing the sequence of the ADAM8 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

ADAM8 polypeptide fragments are provided herein. Such fragments may be truncated at the N-terminus or C-terminus, or may lack internal residues, for example, when compared with a full-length native protein. Certain fragments lack amino acid residues that are not essential for a desired biological activity of the ADAM8 polypeptide.

ADAM8 fragments may be prepared by any of a number of conventional techniques. Desired peptide fragments may be chemically synthesized. An alternative approach involves generating ADAM8 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, ADAM8 polypeptide fragments share at least one biological and/or immunological activity with the native ADAM8 polypeptide.

In particular embodiments, conservative substitutions of interest are shown in Table 3 under the heading of preferred substitutions. If such substitution result in a change in biological activity, then more substantial changes, denominated exemplary substitutions in Table 3, or as further described below in reference to amino acid classes are introduced and the products screened.

TABLE 3

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |

TABLE 3-continued

| Original Residue | Exemplary Substitutions | Preferred Substitutions |
| --- | --- | --- |
| Tyr (Y) | trp; phe; thr; ser | phe |
| Val (V) | ile; leu; met; phe; ala; norleucine | leu |

Substantial modifications in function or immunological identity of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PEACH variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of ADAM8

Covalent modifications of ADAM8 are included within the scope of this invention. One type of covalent modification includes reacting targeted amino acid residues of an ADAM8 polypeptide with an organic derivatizing agent that is capable of reacting with selected side chains or the N- or C-terminal residues of the ADAM8. Derivatization with bifunctional agents is useful, for instance, for crosslinking ADAM8 to a water-insoluble support matrix or surface for use in the method for purifying anti-ADAM8 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the—amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the ADAM8 polypeptide included within the scope of this invention comprises altering the native glycosylation pattern of the polypeptide. "Altering the native glycosylation pattern" is intended for purposes herein to mean deleting one or more carbohydrate moieties found in native sequence ADAM8 (either by removing the underlying glycosylation site or by deleting the glycosylation by chemical and/or enzymatic means), and/or adding one or more glycosylation sites that are not present in the native sequence ADAM8. In addition, the phrase includes qualitative changes in the glycosylation of the native proteins, involving a change in the nature and proportions of the various carbohydrate moieties present.

Addition of glycosylation sites to the ADAM8 polypeptide may be accomplished by altering the amino acid sequence. The alteration may be made, for example, by the addition of, or substitution by, one or more serine or threonine residues to the native sequence ADAM8 (for O-linked glycosylation sites). The ADAM8 amino acid sequence may optionally be altered through changes at the DNA level, particularly by mutating the DNA encoding the ADAM8 polypeptide at preselected bases such that codons are generated that will translate into the desired amino acids.

Another means of increasing the number of carbohydrate moieties on the ADAM8 polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the ADAM8 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of ADAM8 comprises linking the ADAM8 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The ADAM8 of the present invention may also be modified in a way to form a chimeric molecule comprising ADAM8 fused to another, heterologous polypeptide or amino acid sequence.

In one embodiment, such a chimeric molecule comprises a fusion of the ADAM8 with a tag polypeptide that provides an epitope to which an anti-tag antibody can selectively bind. The epitope tag is generally placed at the amino- or carboxyl-terminus of the ADAM8. The presence of such epitope-tagged forms of the ADAM8 can be detected using an antibody against the tag polypeptide. Also, provision of the epitope tag enables the ADAM8 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evans et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an -tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule may comprise a fusion of the ADAM8 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an ADAM8 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of ADAM8

The description below relates primarily to production of ADAM8 by culturing cells transformed or transfected with a vector containing ADAM8 nucleic acid. It is, of course, contemplated that alternative methods, which are well known in the art, may be employed to prepare ADAM8. For instance, the ADAM8 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the ADAM8 may be chemically synthesized separately and combined using chemical or enzymatic methods to produce the full-length ADAM8.

a. Isolation of DNA Encoding an ADAM8 Polypeptide

DNA encoding ADAM8 may be obtained from a cDNA library prepared from tissue believed to possess the ADAM8 mRNA and to express it at a detectable level. Accordingly, human ADAM8 DNA can be conveniently obtained from a cDNA library prepared from human tissue, such as described in the Examples. ADAM8 encoding gene may also be obtained from a genomic library or by oligonucleotide synthesis.

Libraries can be screened with probes (such as antibodies to the ADAM8 polypeptide, or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding ADAM8 is to use PCR methodology [Sambrook et al., supra; Dieffenbach et al., PCR Primer: A Laboratory Manual (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

b. Selection and Transformation of Host Cells

Host cells are transfected or transformed with expression or cloning vectors described herein for ADAM8 production and cultured in conventional nutrient media modified as appropriate for inducing promoters, selecting transformants, or amplifying the genes encoding the desired sequences. The skilled artisan without undue experimentation can select the culture conditions, such as media, temperature, pH and the like. In general, principles, protocols, and practical techniques for maximizing the productivity of cell cultures can be found in *Mammalian Cell Biotechnology: a Practical Approach,* M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology,* 52:456–457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa,* and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for ADAM8-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943, 529; Fleer et al., *Bio/Technology,* 9: 968–975 (1991)) such as, e.g., *K. lactis* (MW98-8C, CBS683, CBS4574; Louvencourt et al., *J. Bacteriol.,* 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Vanden Berg et al., *Bio/Technology,* 8:135 (1990)), *K. thermotolerans,* and *K. marxianus; yarrowia* (EP 402,226); *Pichia pastoris* (EP 183,070; Sreekrishna et al., *J. Basic Microbiol.,* 28:265–278 [1988]); *Candida; Trichoderma reesia* (EP 244,234); *Neurospora crassa* (Case et al., *Proc. Natl. Acad. Sci. USA,* 76:5259–5263 [1979]); *Schwan-*

*niomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284–289 [1983]; Tilburn et al., *Gene,* 26:205–221 [1983]; Yelton et al., *Proc. Natl. Acad. Sci. USA,* 81:1470–1474 [1984]) and *A. niger* (Kelly and Hynes, *EMBO J.,* 4:475–479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs,* 269 (1982).

Suitable host cells for the expression of glycosylated ADAM8 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

c. Selection and Use of a Replicable Vector

The nucleic acid (e.g., cDNA or genomic DNA) encoding ADAM8 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques that are known to the skilled artisan.

The ADAM8 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the ADAM8-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces*—factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the ADAM8-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the ADAM8-encoding nucleic acid sequence to direct mRNA synthesis. Promoters recognized by a variety of potential host cells are well known. Promoters suitable for use with prokaryotic hosts include the beta-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding ADAM8.

Examples of suitable promoting sequences for use with yeast hosts include the promoters for 3-phosphoglycerate kinase [Hitzeman et al., *J. Biol Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

ADAM8 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Inserting an enhancer sequence into the vector may increase transcription of a DNA encoding the ADAM8 by higher eukaryotes. Enhancers are cis-acting elements of DNA, usually about from 10 to 300 bp, that act on a promoter to increase its transcription. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the ADAM8 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding ADAM8.

Still other methods, vectors, and host cells suitable for adaptation to the synthesis of ADAM8 in recombinant vertebrate cell culture are described in Gething et al., *Nature*, 293:620–625 (1981); Mantei et al., *Nature*, 281:40–46 (1979); EP 117,060; and EP 117,058.

d. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence ADAM8 polypeptide or against a synthetic peptide based on the DNA sequences provided herein or against exogenous sequence fused to ADAM8 DNA and encoding a specific antibody epitope.

e. Purification of Polypeptide

Forms of ADAM8 may be recovered from culture medium or from host cell lysates. If membrane-bound, it can be released from the membrane using a suitable detergent solution (e.g., Triton®-X 100) or by enzymatic cleavage. Cells employed in expression of ADAM8 can be disrupted by various physical or chemical means, such as freeze-thaw cycling, sonication, mechanical disruption, or cell lysing agents.

It may be desired to purify ADAM8 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex® G-75; protein A Sepharose® columns to remove contaminants such as IgG; and metal chelating columns to bind epitope-tagged forms of the ADAM8. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular ADAM8 produced.

E. Amplification of Genes Encoding the ADAM8 Polypeptides in Tumor Tissues and Cell Lines The present invention is based on the identification and characterization of genes that are amplified in certain cancer cells.

The genome of prokaryotic and eukaryotic organisms is subjected to two seemingly conflicting requirements. One is the preservation and propagation of DNA as the genetic information in its original form, to guarantee stable inheritance through multiple generations. On the other hand, cells or organisms must be able to adapt to lasting environmental changes. The adaptive mechanisms can include qualitative or quantitative modifications of the genetic material. Qualitative modifications include DNA mutations, in which coding sequences are altered resulting in a structurally and/or functionally different protein. Gene amplification is a quantitative modification, whereby the actual number of complete coding sequence, i.e., a gene, increases, leading to an increased number of available templates for transcription, an increased number of translatable transcripts, and, ultimately, to an increased abundance of the protein encoded by the amplified gene.

The phenomenon of gene amplification and its underlying mechanisms have been investigated in vitro in several prokaryotic and eukaryotic culture systems. The best-characterized example of gene amplification involves the culture of eukaryotic cells in medium containing variable concentrations of the cytotoxic drug methotrexate (MTX). MTX is a folic acid analogue and interferes with DNA synthesis by blocking the enzyme dihydrofolate reductase (DHFR). During the initial exposure to low concentrations of MTX most cells (>99.9%) will die. A small number of cells survive, and are capable of growing in increasing concentrations of MTX by producing large amounts of DHFR-RNA and protein. The basis of this overproduction is the amplification of the single DHFR gene. The additional copies of the gene are found as extrachromosomal copies in the form of small, supernumerary chromosomes (double minutes) or as integrated chromosomal copies.

Gene amplification is most commonly encountered in the development of resistance to cytotoxic drugs (antibiotics for bacteria and chemotherapeutic agents for eukaryotic cells) and neoplastic transformation. Transformation of a eukaryotic cell as a spontaneous event or due to a viral or chemical/environmental insult is typically associated with changes in the genetic material of that cell. One of the most common genetic changes observed in human malignancies are mutations of the p53 protein. p53 controls the transition of cells from the stationary (G1) to the replicative (S) phase and prevents this transition in the presence of DNA damage. In other words, one of the main consequences of disabling p53 mutations is the accumulation and propagation of DNA damage, i.e., genetic changes. Common types of genetic changes in neoplastic cells are, in addition to point mutations, amplifications and gross, structural alterations, such as translocations.

The amplification of DNA sequences may indicate specific functional requirement as illustrated in the DHFR experimental system. Therefore, the amplification of certain oncogenes in malignancies points toward a causative role of these genes in the process of malignant transformation and maintenance of the transformed phenotype. This hypothesis has gained support in recent studies. For example, the bcl-2 protein was found to be amplified in certain types of non-Hodgkin's lymphoma. This protein inhibits apoptosis and leads to the progressive accumulation of neoplastic cells. Members of the gene family of growth factor receptors have been found to be amplified in various types of cancers suggesting that overexpression of these receptors may make neoplastic cells less susceptible to limiting amounts of available growth factor. Examples include the amplification of the androgen receptor in recurrent prostate cancer during androgen deprivation therapy and the amplification of the growth factor receptor homologue ERB2 in breast cancer. Lastly, genes involved in intracellular signaling and control of cell cycle progression can undergo amplification during malignant transformation. This is illustrated by the amplification of the bcl-I and ras genes in various epithelial and lymphoid neoplasms.

These earlier studies illustrate the feasibility of identifying amplified DNA sequences in neoplasms, because this approach can identify genes important for malignant transformation. The case of ERB2 also demonstrates the feasibility from a therapeutic standpoint, since transforming proteins may represent novel and specific targets for tumor therapy.

Several different techniques can be used to demonstrate amplified genomic sequences. Classical cytogenetic analysis of chromosome spreads prepared from cancer cells is adequate to identify gross structural alterations, such as translocations, deletions and inversions. Amplified genomic regions can only be visualized, if they involve large regions with high copy numbers or are present as extrachromosomal material. While cytogenetics was the first technique to demonstrate the consistent association of specific chromosomal changes with particular neoplasms, it is inadequate for the identification and isolation of manageable DNA sequences. The more recently developed technique of comparative genomic hybridization (CGH) has illustrated the widespread phenomenon of genomic amplification in neoplasms. Tumor and normal DNA are hybridized simultaneously onto metaphases of normal cells and the entire genome can be screened by image analysis for DNA sequences that are present in the tumor at an increased frequency. (WO 93/18,186; Gray et al., Radiation Res. 137:275–289 [1994]). As a screening method, this type of analysis has revealed a large number of recurring amplicons (a stretch of amplified DNA) in a variety of human neoplasms. Although CGH is more sensitive than classical cytogenetic analysis in identifying amplified stretches of DNA, it does not allow a rapid identification and isolation of coding sequences within the amplicon by standard molecular genetic techniques.

The most sensitive methods to detect gene amplification are polymerase chain reaction (PCR)-based assays. These assays utilize very small amount of tumor DNA as starting material, are exquisitely sensitive, provide DNA that is amenable to further analysis, such as sequencing and are suitable for high-volume throughput analysis.

The above-mentioned assays are not mutually exclusive, but are frequently used in combination to identify amplifications in neoplasms. While cytogenetic analysis and CGH represent screening methods to survey the entire genome for amplified regions, PCR-based assays are most suitable for the final identification of coding sequences, i.e. genes in amplified regions.

According to the present invention, such genes have been identified by quantitative PCR (S. Gelmini et al., Clin. Chem. 43:752 [1997]), by comparing DNA from a variety of primary tumors, including breast, lung, colon, prostate, brain, liver, kidney, pancreas, spleen, thymus, testis, ovary, uterus, etc. tumor, or tumor cell lines, with pooled DNA from healthy donors. Quantitative PCR was performed using a TaqMan® instrument (ABI Prism®). Gene-specific primers and fluorogenic probes were designed based upon the coding sequences of the DNAs.

Human lung carcinoma cell lines include A549 (SRC768), Calu-1 (SRC769), Calu-6 (SRC770), H157 (SRC771), H441 (SRC772), H460 (SRC773), H522 (SRC832), H810 (SRC833), SKMES-1 (SRC774) and SW900 (SRC775), all available from ATCC. Primary human lung tumor cells usually derive from adenocarcinomas, squamous cell carcinomas, large cell carcinomas, non-small cell carcinomas, small cell carcinomas, and broncho alveolar carcinomas, and include, for example, SRC724 (squamous cell carcinoma abbreviated as "SqCCa")(LT1), SRC725 (non-small cell carcinoma, abbreviated as "NSCCa")(LT1a), SRC726 (adenocarcinoma, abbreviated as "AdenoCa") (LT2), SRC727 (adenocarcinoma)(LT3), SRC728 (squamous cell carcinoma)(LT4), SRC729 (adenocarcinoma) (LT6), SRC730 (adeno/squamous cell carcinoma)(LT7), SRCC731 (adenocarcinoma)(LT9), SRC732 (squamous cell carcinoma)(LT10), SRC733 (adenocarcinoma)(LT11), SRC734 (adenocarcinoma)(LT12), SRC735 (broncho alveolar carcinoma, abbreviated as "BAC")(LT13), SRC736 (squamous cell carcinoma)(LT15), SRC737 (squamous cell carcinoma)(LT16), SRC738 (squamous cell carcinoma) (LT17), SRC739 (squamous cell carcinoma)(LT18), SRC740 (squamous cell carcinoma)(LT19), SRC741 (lung cell carcinoma, abbreviated as "LCCa")(LT21), SRC811 (adenocarcinoma)(LT22).

Colon cancer cell lines include, for example, ATCC cell lines SW480 (adenocarcinoma, SRCC776), SW620 (lymph node metastasis of colon adenocarcinoma, SRC777), Colo320 (carcinoma, SRCC778), Colo205 (carcinoma, SRC828), HCC2998 (carcinoma, SRC830), HT29 (adenocarcinoma, SRC779), HM7 (carcinoma, SRC780), KM12 (carcinoma, SRC831), CaWiDr (adenocarcinoma, SRC781), HCT15 (carcinoma, SRC829), HCT116 (carcinoma, SRC782), SKCO1 (adenocarcinoma, SRC783), SW403 (adenocarcinoma, SRC784), LS174T (carcinoma, SRC785), and HM7 (a high mucin producing variant of ATCC colon adenocarcinoma cell line LS 174T, obtained from Dr. Robert Warren, UCSF). Primary colon tumors include colon adenoocarcinomas designated CT1 (SRC751), CT2 (SRC742), CT3 (SRC743), CT4 (SRC752), CT5 (SRC753) CT6 (SRC754), CT7 (SRC755), CT8 (SRC744), CT9 (SRC756), CT10 (SRC745), CT11 (SRC757), CT12 (SRC746), CT14 (SRC747), CT15 (SRC748), CT16 (SRC749), CT17 (SRC750), CT18 (SRCC758).

Human breast carcinoma cell lines include, for example, HBL100 (SRCC759), MB435s (SRCC760), T47D (SRCC761), MB468 (SRCC762), MB175 (SRCC763), MB361 (SRCC764), BT20 (SRCC765), MCF7 (SRCC766), SKBR3 (SRCC767).

F. Tissue Distribution

The results of the gene amplification assays herein can be verified by further studies, such as, by determining mRNA expression in various human tissues.

As noted before, gene amplification and/or gene expression in various tissues may be measured by conventional Southern blotting, Northern blotting to quantitate the transcription of mRNA (Thomas, *Proc. Natl. Acad. Sci. USA,* 77:5201–5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence ADAM8 polypeptide or against a synthetic peptide based on the DNA sequences provided herein or against exogenous sequence fused to sequence ADAM8 DNA and encoding a specific antibody epitope. General techniques for generating antibodies, and special protocols for Northern blotting and in situ hybridization are provided hereinbelow.

G. Chromosome Mapping

If the amplification of a given gene is functionally relevant, then that gene should be amplified more than neighboring genomic regions which are not important for tumor survival. To test this, the gene can be mapped to a particular chromosome, e.g. by radiation-hybrid analysis. The amplification level is then determined at the location identified, and at neighboring genomic region. Selective or preferential amplification at the genomic region to which to gene has been mapped is consistent with the possibility that the gene amplification observed promotes tumor growth or survival. Chromosome mapping includes both framework and epicenter mapping. For further details see e.g., Stewart et al., *Genome Research* 7:422–433 (1997).

H. Antibody Binding Studies

The results of the gene amplification study can be further verified by antibody binding studies, in which the ability of anti-ADAM8 to inhibit the biological activity of the ADAM8 polypeptides on tumor (cancer) cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques,* pp.147–158 (CRC Press, Inc., 1987).

Competitive binding assays rely on the ability of a labeled standard to compete with the test sample analyte for binding with a limited amount of antibody. The amount of target protein (encoded by a gene amplified in a tumor cell) in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, a first antibody that is immobilized on a solid support binds the test sample analyte, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

I. Cell-Based Tumor Assays

Cell-based assays and animal models for tumors (e.g., cancers) can be used to verify the findings of the gene amplification assay, and further understand the relationship between the genes identified herein and the development and pathogenesis of neoplastic cell growth. The role of gene products identified herein in the development and pathology of tumor or cancer can be tested by using primary tumor cells or cells lines that have been identified to amplify the genes herein. Such cells include, for example, the breast, colon and lung cancer cells and cell lines listed above.

In a different approach, cells of a cell type known to be involved in a particular tumor are transfected with the cDNAs herein, and the ability of these cDNAs to induce excessive growth is analyzed. Suitable cells include, for example, stable tumor cells lines such as, the B104-1-1 cell line (stable NIH-3T3 cell line transfected with the neu protooncogene) and ras-transfected NIH-3T3 cells, which can be transfected with the desired gene, and monitored for tumorogenic growth. Such transfected cell lines can then be used to test the ability of poly- or monoclonal antibodies or antibody compositions to inhibit tumorogenic cell growth by exerting cytostatic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cancer.

In addition, primary cultures derived from tumors in transgenic animals (as described below) can be used in the cell-based assays herein, although stable cell lines are preferred. Techniques to derive continuous cell lines from transgenic animals are well known in the art (see, e.g., Small et al., *Mol. Cell. Biol.* 5:642–648 [1985]).

J. Animal Models

A variety of well known animal models can be used to further understand the role of the genes identified herein in the development and pathogenesis of tumors, and to test the efficacy of candidate therapeutic agents, including antibodies, and other antagonists of the native polypeptides, including small molecule antagonists. The in vivo nature of such models makes them particularly predictive of responses in human patients. Animal models of tumors and cancers (e.g. breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g. subcutaneous injection, tail vein injection, spleen implantation, intraperitoneal implantation, implantation under the renal capsule, or orthopin implantation, e.g. colon cancer cells implanted in colonic tissue. (See, e.g. PCT publication No. WO 97/33551, published Sep. 18, 1997).

Probably the most often used animal species in oncological studies are immunodeficient mice and, in particular, nude mice. The observation that the nude mouse with hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g., *The Nude Mouse in Oncology Research*, E. Boven and B. Winograd, eds., CRC Press, Inc., 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well-differentiated grade II human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer* 48:689–696 [1983]).

Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra.

Animal models of breast cancer can be generated, for example, by implanting rat neuroblastoma cells (from which the neu oncogen was initially isolated), or neu-transformed NIH-3T3 cells into nude mice, essentially as described by Drebin et al. *PNAS USA* 83:9129–9133 (1986).

Similarly, animal models of colon cancer can be generated by passaging colon cancer cells in animals, e.g. nude mice, leading to the appearance of tumors in these animals. An orthotopic transplant model of human colon cancer in nude mice has been described, for example, by Wang et al., *Cancer Research* 54:4726–4728 (1994) and Too et al., *Cancer Research* 55:681–684 (1995). This model is based on the so-called "METAMOUSE") sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.* 146:720 [1977]), which provide a highly controllable model system for studying the anti-tumor activities of various agents (Palladino et al., *J. Immunol.* 138:4023–4032 [1987]). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animal are then infected subcutaneously with 10 to 100 μl of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer* 41:suppl. 4:309 [1980]), and evidence indicates that tumors can be started from injection of even a single cell and that a very high proportion of infected tumor cells survive. For further information about this tumor model see Zacharski, *Haemostasis* 16:300–320 [1986]).

One way of evaluating the efficacy of a test compound in an animal model is implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals*, Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals.

Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82:6148–615 [1985]); gene targeting in embryonic stem cells (Thompson et al., *Cell* 56:313–321 [1989]); electroporation of embryos (Lo, *Mol. Cell Biol.* 3:1803–1814 [1983]); sperm-mediated gene transfer (Lavitrano et al., *Cell* 57:717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89:6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock out" animals can be constructed which have a defective or altered gene encoding an ADAM8 polypeptide identified herein, as a result of homologous recombination between the endogenous gene encoding the polypeptide and altered genomic DNA encoding the same polypeptide introduced into an embryonic cell of the animal. For example, cDNA encoding an ADAM8 polypeptide can be used to clone genomic DNA encoding that polypeptide in accordance with established techniques. A portion of the genomic DNA encoding a particular ADAM8 polypeptide can be deleted or replaced with another gene, such as a gene encoding a selectable marker that can be used to monitor integration. Typically, several kilobases of unaltered flanking DNA (both at the 5' and 3' ends) are included in the vector [see e.g., Thomas and Capecchi, *Cell* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, by their ability to defend against certain pathological conditions and by their development of pathological conditions due to absence of the ADAM8 polypeptide.

The efficacy of antibodies specifically binding the polypeptides identified herein and other drug candidates can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is limited by the rare occurrence of this type of tumor in animals.

K. Screening Assays for Drug Candidates

Screening assays for drug candidates are designed to identify compounds that bind or complex with the polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein-binding assays, biochemical-screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular ADAM8 polypeptide encoded by a gene identified herein, its interaction with that polypeptide can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* 340: 245–246 (1989); Chien et al., *Proc. Natl. Acad. Sci. USA* 88: 9578–9582 (1991)] as disclosed by Chevray and Nathans, *Proc. Natl. Acad. Sci. USA* 89:5789–5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for beta-galactosidase. A complete kit (MATCHMAKFR™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of an ADAM8-encoding gene identified herein and other intra- or extracellular components can be tested as follows: usually a reaction mixture is prepared containing the product of the amplified gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

L. Compositions and Methods for the Treatment of Tumors

The compositions useful in the treatment of tumors associated with the amplification of the genes identified herein include, without limitation, antibodies, small organic and inorganic molecules, peptides, phosphopeptides, antisense and ribozyme molecules, triple helix molecules, etc. that inhibit the expression and/or activity of the target gene product.

For example, antisense RNA and RNA molecule act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4:469–471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g. PCT publication No. WO 97/33551, supra.

These molecules can be identified by any or any combination of the screening assays discussed hereinabove and/or by any other screening techniques well known for those skilled in the art.

M. Antibodies

Some of the most promising drug candidates according to the present invention are antibodies and antibody fragments that inhibit the production or the gene product of the amplified genes identified herein and/or reduce the activity of the gene products.

1. Polyclonal Antibodies

The skilled artisan knows methods of preparing polyclonal antibodies. One can raise polyclonal antibodies in a mammal, for example, or more injections of an immunizing agent and, if desired an adjuvant. Typically, the immunizing agent and/or adjuvant will be injected in the mammal by multiple subcutaneous or intraperitoneal injections. The immunizing agent may include the ADAM8 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

2. Monoclonal Antibodies

The anti-ADAM8 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the ADAM8 polypeptide, including fragments, or a fusion protein of such protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection (ATCC), Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against ADAM8. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose®, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-ADAM8 antibodies may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, corresponding non-human residues replace Fv framework residues of the human immunoglobulin. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*

321:522–525 (1986); Riechmann et al., *Nature* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321:522–525 (1986); Riechmann et al., *Nature* 332:323–327 (1988); Verhoeyen et al., *Science* 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.* 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779–783 (1992); Lonberg et al., *Nature* 368:856–859 (1994); Morrison, *Nature* 368:812–13 (1994); Fishwild et al., *Nature Biotechnology* 14:845–51 (1996); Neuberger, *Nature Biotechnology* 14:826 (1996); Lonberg and Huszar, *Intern. Rev. Immunol.* 13:65–93 (1995).

4. Antibody Dependent Enzyme Mediated Prodrug Therapy (ADEPT)

The antibodies of the present invention may also be used in ADEPT by conjugating the antibody to a prodrug-activating enzyme that converts a prodrug (e.g., a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such as way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug 5-fluorouracil; proteases, such as serratia protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as—galactosidase and neuraminidase useful for converting glycosylated prodrugs into free drugs; beta-lactamase useful for converting drugs derivatized with beta-lactams into free drugs; and penicillin amidases, such as penicillin Vamidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328:457–458 (1987)). Antibody-abzyme conjugates can be prepared as described herein for delivery of the abzyme to a tumor cell population.

The enzymes of this invention can be covalently bound to the anti-ADAM8 antibodies by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312:604–608 (1984)).

5. Bispecific Antibodies

Bispecific antibodies are monoclonal, preferably human or humanized, antibodies that have binding specificities for at least two different antigens. In the present case, one of the binding specificities is for the ADAM8, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature* 305:537–539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology* 121:210 (1986).

According to another approach described in WO 96/27011, the interface between a pair of antibody molecules can be engineered to maximize the percentage of heterodimers that are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as triggers the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given polypeptide herein. Alternatively, an anti-polypeptide arm may be combined with an arm which binds to a triggering molecule on a leukocyte such as a T-cell receptor molecule (e.g., CD2, CD3, CD28, or B7), or Fc receptors for IgG (Fc R), such as Fc RI (CD64), Fc RII (CD32) and Fc RIII (CD 16) so as to focus cellular defense mechanisms to the cell expressing the particular polypeptide. Bispecific antibodies may also be used to localize cytotoxic agents to cells that express a particular polypeptide. These antibodies possess a polypeptide-binding arm and an arm that binds a cytotoxic agent or a radionuclide chelator, such as EOTUBE, DPTA, DOTA, or TETA. Another bispecific antibody of interest binds the polypeptide and further binds tissue factor (TF).

6. Heteroconjugate Antibodies

Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, *J. Immunol.* 148:2918–2922 (1992). Homodimeric antibodies with enhanced anti-tumor activity may also be prepared using heterobifunctional cross-linkers as described in Wolff et al. *Cancer Research* 53:2560–2565 (1993). Alternatively, an antibody can be engineered which has dual Fc regions and may thereby have enhanced complement lysis and ADCC capabilities. See Stevenson et al., *Anti-Cancer Drug Design* 3:219–230 (1989).

8. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant or animal origin, or fragments thereof, or a small molecule toxin), or a radioactive isotope (i.e., a radioconjugate).

Chemotherapeutic agents useful in the generation of such immunoconjugates have been described above. Enzymatically active protein toxins and fragments thereof which can be used include diphtheria A chain, nonbinding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, saporin, mitogellin, restrictocin, phenomycin, enomycin and the tricothecenes. Small molecule toxins include, for example, calicheamicins (U.S. Pat. No. 5,053,394), maytansinoids (U.S. Pat. No. 5,208,020), palytoxin and CC1065. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

9. Immunoliposomes

The antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286–288 (1982) via a disulfide interchange reaction. A chemotherapeutic agent (such as Doxorubicin) is optionally contained within the liposome. See Gabizon et al., *J. National Cancer Inst.* 81(19):1484 (1989).

10. Pharmaceutical Compositions

Antibodies specifically binding the product of an amplified gene identified herein, as well as other molecules identified by the screening assays disclosed hereinbefore, can be administered for the treatment of tumors, including cancers, in the form of pharmaceutical compositions.

If the protein encoded by the amplified gene is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90:7889–7893 [1993]).

Therapeutic formulations of the antibody are prepared for storage by mixing the antibody having the desired degree of purity with optional pharmaceutically acceptable carriers, excipients or stabilizers (*Remington's Pharmaceutical Sciences*, 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Non-antibody compounds identified by the screening assays of the present invention can be formulated in an analogous manner, using standard techniques well known in the art.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

11. Methods of Treatment

It is contemplated that the antibodies and other anti-tumor compounds of the present invention may be used to treat various conditions, including those characterized by overexpression and/or activation of the amplified genes identified herein. Exemplary conditions or disorders to be treated with such antibodies and other compounds, including, but not limited to, small organic and inorganic molecules, peptides, antisense molecules, etc., include benign or malignant tumors (e.g., renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The anti-tumor agents of the present invention, e.g., antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the anti-cancer agents, e.g., antibodies of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the anti-tumor agent, e.g., antibody, or may be given simultaneously therewith. The antibody may be combined with an anti-oestrogen compound such as tamoxifen or an anti-progesterone such as onapristone (see, EP 616812) in dosages known for such molecules.

It may be desirable to also administer antibodies against other tumor associated antigens, such as antibodies which bind to the ErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent, e.g., an antibody herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

For example, depending on the type and severity of the disease, about 1 µg/kg to 15 mg/kg (e.g., 0.1–20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

In addition, an agent that inhibits the activity of ADAM8 can be used to diagnose or treat various diseases of inflammation. Initiating, exacerbating, or ongoing events in diseases of both acute and chronic inflammation involve the trafficking and migration of various populations of leukocytes, for example monocytes, into and out of tissue resulting in tissue damage. Inhibiting the migration, trafficking, and tissue destruction by leukocytes by inhibiting ADAM8 mitigates the inflammatory process. Diseases such as psoriasis, dermatitis, inflammatory bowel disease, arthritis, multiple sclerosis and chronic obstructive pulmonary diseases are examples of diseases, which can be treated, with an inhibitor of ADAM8.

Additional examples of such diseases include T cell inflammatory responses such as inflammatory skin diseases including responses associated with inflammatory bowel disease (such as Crohn's disease and ulcerative colitis); adult respiratory distress syndrome; meningitis; encephalitis; uveitis; allergic conditions such as eczema and asthma; conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; chronic obstructive pulmonary disease (COPD); bronchitis; insulinitis; rhinitis; urticaria; glomerulonephritis; diseases involving leukocyte diapedesis; CNS inflammatory disorder; multiple organ injury syndrome secondary to septicaemia or trauma; autoimmune hemolytic anemia; myethemia gravis; antigen-antibody complex mediated diseases; nephrotic syndrome; malignancies (e.g., B-cell malignancies such as chronic lymphocytic leukemia or hairy cell leukemia); all types of transplantations, including graft vs. host or host vs. graft disease; HIV and rhinovirus infection; pulmonary fibrosis; invasion of tumor cells into secondary organs etc.

These diseases can be treated using the formulations, routes of administration, doses and dosing formats discussed above for use in anti-tumor settings.

12. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent that is capable of interfering with the activity of a gene product identified herein, e.g., an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

13. Diagnosis and Prognosis of Tumors

While cell surface proteins, such as growth receptors overexpressed in certain tumors are excellent targets for drug candidates or tumor (e.g., cancer) treatment, the same proteins along with secreted proteins encoded by the genes amplified in tumor cells find additional use in the diagnosis and prognosis of tumors. For example, antibodies directed against the proteins products of genes amplified in tumor cells can be used as tumor diagnostics or prognostics.

For example, antibodies, including antibody fragments, can be used to qualitatively or quantitatively detect the expression of proteins encoded by the amplified genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the amplified gene encodes a cell surface protein, e.g., a growth factor. Such binding assays are performed essentially as described in section 5 above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Blvd., Manassas, Va. 20110-2209. Unless otherwise noted, the present invention uses standard procedures of recombinant DNA technology, such as those described hereinabove and in the following textbooks: Sambrook et al., *Molecular Cloning: A Laboratory Manual*, Cold Spring Harbor Press N.Y., 1989; Ausubel et al., *Current Protocols in Molecular Biology*, Green Publishing Associates and Wiley Interscience, N.Y., 1989; Innis et al., *PCR Protocols: A Guide to Methods and Applications*, Academic Press, Inc., N.Y., 1990; Harlow et al., *Antibodies: A Laboratory Manual*, Cold Spring Harbor Press, Cold Spring Harbor, 1988; Gait, *Oligonucleotide Synthesis*, IRL Press, Oxford, 1984; R. I. Freshney, *Animal Cell Culture*, 1987; Coligan et al., *Current Protocols in Immunology*, 1991.

Example 1

Gene Amplification

This example shows that ADAM8 mRNA is present at higher levels in cells of certain breast, lung, and colon cancers. An increase in the level of mRNA is indicative of an increase in the amount of the ADAM8 protein expressed on the surface of cells. A protein that is overexpressed in certain cancers such as colon, breast, lung and other cancers is a useful target for therapeutic intervention. Therapeutic agents may take the form of antagonists of ADAM8 polypeptide, for example, murine-human chimeric, humanized or human antibodies against an ADAM8-polypeptide.

The starting material for the screen was total RNA isolated from thinly sliced frozen sections of a variety of cancers. The total RNA is quantitated spectrophotometrically. As a means of comparison, RNA was also isolated from normal healthy tissue removed from nearby each of the tumors. Real-time quantitative PCR (ABI Prism® 7700 Sequence Detection System, PerkinElmer®, Applied Biosystems Division, Foster City, Calif.) was used to find differences in the mRNA levels in the tumor tissue versus the normal tissue. The results were used to determine whether the DNA encoding ADAM8 is over-represented in any of the primary lung, colon or breast cancers that were screened.

The results of the Taqman™ analysis are reported in delta ($\Delta$) Ct units. One unit corresponds to 1 PCR cycle of approximately a 2-fold increase relative to the normal tissue, 2 units corresponds to a 4-fold, 3 units to an 8-fold increase and so on. Quantitation was obtained using primers and a Taqman™ fluorescent probe derived from the ADAM8-encoding gene. Regions that are more likely to contain unique nucleic acid sequences that are least likely to have splice out introns are preferred for the primer and probe derivation, e.g. 3'-untranslated regions. Two sets of primer/probe combinations were used for the Taqman™ analysis. The sequences for the primers and probe used for the ADAM8 mRNA analysis were as follows:

```
Set1—a primer/probe set which amplifies a portion
         of the 3'-untranslated region
```

```
                          -continued
forward primer
                                          (SEQ ID NO:3)
8-2570F (22mer)       GCTCAGCCCTAGACCCTGACTT probe
                                          (SEQ ID NO:4)
8-2594T (32mer)       CAGGCTCAGCTGCTGTTCTAACCTCAGTA
                                                    ATG reverse primer
                                          (SEQ ID NO:5)
8-2655R (18mer)       CGTGGACAGCAGGAGCCT Set2-a primer/probe set which amplifies a portion
               of the coding sequence
forward primer
                                          (SEQ ID NO:6)
ADAM8.3-1797F (19mer) TTGCTGGAAAGGACGTTGC probe
                                          (SEQ ID NO:7)
ADAM8.3-1817T (32mer) AGGACTTACACGTTTACAGATCCAGCAAC
                                                    TGC reverse primer
                                          (SEQ ID NO:8)
ADAM8.3-1881R (19mer) GTTGCACACCCCATGGTTG
```

The 5' nuclease procedure is run on a real-time quantitative PCR device such as the ABI Prism® 7700 Sequence Detection System. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The Ct values are used as quantitative measurement of the relative number of starting copies of a particular target sequence in a nucleic acid sample when comparing cancer DNA results to normal human DNA results.

RNA Preparation and Quantitation

RNA was prepared from thinly sliced section of frozen matched human tumor and normal tissue. The isolation was preformed using purification kit, including buffers, columns, and other reagents from Qiagen RNeasy® mini kits according to the manufacturer s instructions and the description below.

Prior to beginning, 10 µl of beta-mercaptoethanol was added to every 1 ml of buffer RLT. One to four 10 or 20 µ-sections of each tumor and normal tissue were cut from a tissue block using a cryostat. These sections were placed immediately into a 1.5 ml microcentrifuge tube containing 350 or 600 µl of buffer RLT to which beta-mercaptoethanol had been added. The tissue sections were homogenized for approximately 30 seconds using a VerTis hand-held homogenizer with a generator small enough to fit into a 1.5 ml microcentrifuge tube. The generator was cleaned by operating it in sterile $H_2O$ for approximately 10 seconds, 0.1% SDS for approximately 10 seconds, and again in sterile $H_2O$ for approximately 10 seconds. This was done prior to processing the first tissue sample and again in between every tissue sample. The 1.5 ml microcentrifuge tubes containing the homogenized samples were spun for 3 minutes at maximum speed in a microfuge. The supernatant was transferred to a fresh microcentrifuge tube. Each sample was then drawn into and ejected from a 3 cc syringe with a 22 ga needle 20 times. The purpose of this added step is to shear any genomic DNA that may be in the sample after the homogenization and microfuge spin. Then one volume (usually either 350 or 600 µl) of 70% ethanol was added to each sample and mixed by pipetting. A RNeasy® mini spin column sitting in a 2 ml collection tube was loaded with 700 µl of sample. The column was centrifuged for 15 seconds at least 8000×g. If the volume of the sample exceeded 700 µl, then successive aliquots were loaded onto the RNeasy® mini column and it was centrifuged again as above. After each centrifuge spin the flow-through was discarded. This same column was loaded with 700 µl of buffer RW1 and centrifuged for 15 seconds at least 8000×g to wash the column. The RNeasy® mini column was transferred to a new 2-ml collection tube and loaded with 500 µl of Buffer RPE and centrifuged for 15 seconds at least 8000.times.g to wash the column. The flow-through was discarded and the collection tube was reused. The column was loaded with 500 µl of Buffer RPE and centrifuged for 2 minutes at maximum speed to dry the RNeasy® membrane. The RNeasy® column was transferred to a new 1.5 ml collection tube and loaded with 30–50 µl of RNase-free water applied directly to the column membrane. The column was centrifuged for 1 minute at least 8000×g to elute the RNA.

RNA was quantified by standard A260, A280 spectrophotometry on a 1:20 or 1:25 dilution of the eluted sample into $H_2O$. Diluted samples were placed in 0.1 ml quartz cuvettes and read in a Beckman DU640 spectrophotometer.

Gene Amplification Assay

The ADAM8 primer/probe sets were used in Taqman™ analysis to amplify the ADAM8 mRNA in the total RNA samples prepared from human breast, lung and colon tumors and compared with normal tissue sections taken from nearby the tumors. The total RNA was diluted to 2.5 ng/µl in $H_2O$. The samples were tested in duplicate or triplicate and included on the plate were reactions with GAPDH and/or b-actin Taqman™ primers and probe, no template controls, and no reverse transcriptase controls. The reactions were prepared as follows:

```
   10 µl   25 mM MgCl2 (Perkin Elmer reagent)
    5 µl   10X Buffer A (Perkin Elmer reagent)
    6 µl   10 mM dNTPs (Perkin Elmer reagent)
  0.5 µl   Forward Primer (1 OD/100 µl)
  0.5 µl   Reverse Primer (1 OD/100 µl)
  2.5 µl   Probe (2 µM)
    1 µl   RNase Inhibitor 20 units/µl (Perkin Elmer reagent)
 0.25 µl   MuLV Reverse Transcriptase 50 units/µl (Perkin Elmer reagent)
  0.5 µl   TaqGold Taq Polymerase 5 units/µl (Perkin Elmer reagent)
13.75 µl   H2O
   10 µl   total RNA 2.5 ng/µl
```

Reactions were prepared in 96 well plates (MicroAmp™Optical reaction plates, N801-0560, PerkinElmer®). Plates were placed in the PerkinElmer® 7700 Sequence Detection System and the instrument was programmed for the following temperatures and times:
48° 30 minutes (reverse transcription of mRNA)
95° 10 minutes (activation of TaqGold)
40 cycles of the following (amplification of specific mRNA):
95° 15 seconds
60° 1 minute Data analysis was done on the Sequence Detection System software and calculation on Excel and differences were reported as delta (Δ) Ct between tumor and normal.

Results

Increase in ADAM8 mRNA versus normal tissue:
Breast tumor: 5×
Breast tumor: 1600×
Lung tumor: 4.6×
Colon tumor: 3.4×
Colon tumor margin: 2.2×

In additional experiments, quantitation was done initially by the spectrophotometric method, RNA samples were run in Taqman™ experiments, and then the diluted RNA samples were again quantitated using the RiboGreen® RNA Quantitation Kit (Molecular Probes R-11490) following manufacturer's directions. Plates were read on a fluorescent plate reader (SpectraMax® Gemini, Molecular Devices). Samples were diluted using the spectrophotometric readings to 2.5 ng/μl. After Taqman™ experiments were run, Ct values were adjusted for any differences in RNA concentration as determined by the fluorescent quantitation method.

Additionally, it was determined that more accurate data was obtained by not normalizing to another gene. The colon tumor sample reported above was rerun using these additional methods and several other samples are reported below.

Increase in ADAM8 mRNA versus normal tissue:
Colon tumor: 10× (rerun)
Colon tumor margin: 6.8× (rerun)
Colon tumor: 7.4×
Colon tumor: 3.5×
Breast tumor: 4.8×

Example 2

Gene Amplification

This example shows that the ADAM8-encoding genes are amplified in the genome of certain human lung, colon and/or breast cancers and/or cell lines. Amplification is associated with overexpression of the gene product, indicating that the polypeptides are useful targets for therapeutic intervention in certain cancers such as colon, lung, breast and other cancers. Therapeutic agents may take the form of antagonists of ADAM8 polypeptide, for example, murine-human chimeric, humanized or human antibodies against an ADAM8 polypeptide.

The starting material for the screen was genomic DNA isolated from a variety of cancers. The DNA is quantitated precisely, e.g., fluorometrically. As a negative control, DNA was isolated from the cells often normal healthy individuals, which was pooled and used as assay controls for the gene copy in healthy individuals (not shown). The 5' nuclease assay (for example, TaqMan™) and real-time quantitative PCR (for example, ABI Prism® 7700 Sequence Detection System (PerkinElmer®, Applied Biosystems Division, Foster City, Calif.)), were used to find genes potentially amplified in certain cancers. The results were used to determine whether the DNA encoding ADAM8 is over-represented in any of the primary lung or colon cancers or cancer cell lines or breast cancer cell lines that were screened. The primary lung cancers were obtained from individuals with tumors of the type and stage as indicated in Table 2. An explanation of the abbreviations used for the designation of the primary tumors listed in Table 2 and the primary tumors and cell lines referred to throughout this example has been given hereinbefore.

The results of the Taqman™ are reported in delta (Δ) CT units. One unit corresponds to 1 PCR cycle or approximately a 2-fold amplification relative to normal, two units corresponds to 4-fold, 3 units to 8-fold amplification and so on. Quantitation was obtained using primers and a Taqman™ fluorescent probe derived from the ADAM8-encoding gene. Regions of ADAM8 which are most likely to contain unique nucleic acid sequences and which are least likely to have spliced out introns are preferred for the primer and probe derivation, e.g., 3-untranslated regions. The sequences for the primers and probes (forward, reverse and probe) used for the ADAM8 gene amplification analysis were as follows:

```
forward primer
                                     (SEQ ID NO:3)
8-2570F (22mer)    GCTCAGCCCTAGACCCTGACTT probe
                                     (SEQ ID NO:4)
8-2594T (32mer)    CAGGCTCAGCTGCTGTTCTAACCTCAGTAATG reverse primer
                                     (SEQ ID NO:5)
8-2655R (18mer)    CGTGGACAGCAGGAGCCT
```

The 5' nuclease is a fluorescent PCR-based technique that makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism® 7700 Sequence Detection System. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The Ct values are used as quantitative measurement of the relative number of starting copies of a particular target sequence in a nucleic acid sample when comparing cancer DNA results to normal human DNA results.

Table 4 describes the stage, T stage and N stage of various primary tumors that were used to screen the ADAM8 compounds of the invention.

The primary lung cancers were obtained from individuals with tumors of the type and stage as indicated in Table 4. An explanation of the abbreviations used for the designation of the primary tumors listed in Table 4 and the primary tumors and cell lines referred to throughout this example has been given hereinbefore.

20 mg/ml and equilibrated at 4° C. 10 mL of G2 Buffer was prepared by diluting Qiagen® RNAse A stock (100 mg/ml) to a final concentration of 200 μg/ml.

Buffer C1 (10 mL, 4° C.) and ddH$_2$O (40 mL, 4° C.) were then added to the 10 mL of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 mL Buffer C1 (at 4° C.) and 6 mL ddH$_2$O, followed by a second 4° C. centrifugation at 2500 rpm for 15 minutes. The nuclei were then resuspended into the residual buffer using 200 μl per tip. G2 buffer (10 ml) was added to the suspended nuclei while gentle vortexing

TABLE 4

Primary Lung and Colon Tumor Profiles

| Primary Tumor | Stage | Other Stage | Dukes Stage | T Stage | N Stage |
|---|---|---|---|---|---|
| Human lung tumor AdenoCa (SRCC724) [LT1] | IIA | | | T1 | N1 |
| Human lung tumor SqCCa (SRCC725) [LT1a] | IIB | | | T3 | N0 |
| Human lung tumor AdenoCa (SRCC726) [LT2] | IB | | | T2 | N0 |
| Human lung tumor AdenoCa (SRCC727) [LT3] | IIIA | | | T1 | N2 |
| Human lung tumor AdenoCa (SRCC728) [LT4] | IB | | | T2 | N0 |
| Human lung tumor SqCCa (SRCC729) [LT6] | IB | | | T2 | N0 |
| Human lung tumor Aden/SqCCa (SRCC730) [LT7] | IA | | | T1 | N0 |
| Human lung tumor AdenoCa (SRCC731) [LT9] | IB | | | T2 | N0 |
| Human lung tumor SqCCa (SRCC732) [LT10] | IIB | | | T2 | N1 |
| Human lung tumor SqCCa (SRCC733) [LT11] | IIA | | | T1 | N1 |
| Human lung tumor AdenoCa (SRCC734) [LT12] | IV | | | T2 | N0 |
| Human lung tumor AdenoSqCCa (SRCC735) [LT13] | IB | | | T2 | N0 |
| Human lung tumor SqCCa (SRCC736) [LT15] | IB | | | T2 | N0 |
| Human lung tumor SqCCa (SRCC737) [LT16] | IB | | | T2 | N0 |
| Human lung tumor SqCCa (SRCC738) [LT17] | IIB | | | T2 | N1 |
| Human lung tumor SqCCa (SRCC739) [LT18] | IB | | | T2 | N0 |
| Human lung tumor SqCCa (SRCC740) [LT19] | IB | | | T2 | N0 |
| Human lung tumor LCCa (SRCC741) [LT21] | IIB | | | T3 | N1 |
| Human lung AdenoCa (SRCC811) [LT22] | 1A | | | T1 | N0 |
| Human colon AdenoCa (SRCC742) [CT2] | | M1 | D | pT4 | N0 |
| Human colon AdenoCa (SRCC743) [CT3] | | | B | pT3 | N0 |
| Human colon AdenoCa (SRCC744) [CT8] | | | B | T3 | N0 |
| Human colon AdenoCa (SRCC745) [CT10] | | | A | pT2 | N0 |
| Human colon AdenoCa (SRCC746) [CT12] | | MO, R1 | B | T3 | N0 |
| Human colon AdenoCa (SRCC747) [CT14] | | pMO, RO | B | pT3 | pN0 |
| Human colon AdenoCa (SRCC748) [CT15] | | M1, R2 | D | T4 | N2 |
| Human colon AdenoCa (SRCC749) [CT16] | | pMO | B | pT3 | pN0 |
| Human colon AdenoCa (SRCC750) [CT17] | | | C1 | pT3 | pN1 |
| Human colon AdenoCa (SRCC751) [CT1] | | MO, R1 | B | pT3 | N0 |
| Human colon AdenoCa (SRCC752) [CT4] | | | B | pT3 | M0 |
| Human colon AdenoCa (SRCC753) [CT5] | | G2 | C1 | pT3 | pN0 |
| Human colon AdenoCa (SRCC754) [CT6] | | pMO, RO | B | pT3 | pN0 |
| Human colon AdenoCa (SRCC755) [CT7] | | G1 | A | pT2 | pN0 |
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | MO, RO | B | pT3 | pN0 |

DNA Preparation:

DNA was prepared from cultured cell lines, primary tumors, normal human blood. The isolation was performed using purification kit, buffer set and protease and all from Qiagen®, according to the manufacturer's instructions and the description below.

Cell Culture Lysis:

Cells were washed and trypsinized at a concentration of $7.5 \times 10^8$ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 mL PBS. Buffer C1 was equilibrated at 4° C. Qiagen® protease #19155 was diluted into 6.25 ml cold ddH$_2$O to a final concentration of was applied. Upon completion of buffer addition, vigorous vortexing was applied for 30 seconds. Qiagen® protease (200 μl, prepared as indicated above) was added and incubated at 50° C. for 60 minutes. The incubation and centrifugation was repeated until the lysates were clear (e.g., incubating additional 30–60 minutes, pelleting at 3000×g for 10 mm 4° C.).

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenized in 19 ml G2 buffer for 60 seconds using the large tip of the polytron in a laminar-flow TC hood to order to avoid inhalation of aerosols, and held at room temperature. Between samples, the polytron was cleaned by spinning at 2×30 seconds each in 2 L ddH$_2$O, followed by G2 buffer (50 ml). If tissue was still present on the generator tip, the apparatus was disassembled and cleaned.

Qiagen® protease (prepared as indicated above, 1.0 ml) was added, followed by vortexing and incubation at 50° C. for 3 hours. The incubation and centrifugation was repeated until the lysates were clear (e.g., incubating additional 30–60 minutes, pelleting at 3000×g for 10 min., 4° C.).

Human Blood Preparation and Lysis:

Blood was drawn from healthy volunteers using standard infectious agent protocols and citrated into 10 ml samples per tip. Qiagen® protease was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddH$_2$O (4° C). Vortexing was repeated until the pellet was white. The nuclei were then suspended into the residual buffer using a 200 µl tip. G2 buffer (10 ml) were added to the suspended nuclei while gently vortexing, followed by vigorous vortexing for 30 seconds. Qiagen® protease was added (200 µl) and incubated at 50° C. for 60 minutes. The incubation and centrifugation was repeated until the lysates were clear (e.g., incubating additional 30–60 minutes, pelleting at 3000×g for 10 mm 4° C.).

Purification of Cleared Lysates:

(1) Isolation of Genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1–2 hours.

(2) Quantitation of Genomic DNA and Preparation for Gene Amplification Assay:

The DNA levels in each tube were quantified by standard A260, A280 spectrophotometry on a 1:20 dilution (5 µl DNA+95 µl ddH$_2$O) using the 0.1 ml quartz cuvettes in the Beckman DU640 spectrophotometer. A260/A280 ratios were in the range of 1.8–1.9. Each DNA samples was then diluted further to approximately 200 ng/ml in TE (pH 8.5). If the original material was highly concentrated (about 700 ng/µl), the material was placed at 50° C. for several hours until resuspended.

Fluorometric DNA quantitation was then performed on the diluted material (20–600 ng/ml) using the manufacturer's guidelines as modified below. This was accomplished by allowing a Hoefer DyNA Quant™ 200 fluorometer to warm-up for about 15 minutes. The Hoechst dye working solution (#H33258, 10 µl, prepared within 12 hours of use) was diluted into 100 ml 1× TNE buffer. A 2 ml cuvette was filled with the fluorometer solution, placed into the machine, and the machine was zeroed. pGEM 3Zf(+) (2 µl, lot #360851026) was added to 2 ml of fluorometer solution and calibrated at 200 units. An additional 2 µl of pGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometrically determined concentration was then used to dilute each sample to 10 ng/ 1 in ddH$_2$O. This was done simultaneously on all template samples for a single TaqMan™ plate assay, and with enough material to run 500–1000 assays. The samples were tested in triplicate with Taqman™ primers and probe both B-actin and GAPDH on a single plate with normal human DNA and no-template controls. The diluted samples were used provided that the CT value of normal human DNA subtracted from test DNA was +/−1CT. The diluted, lot-qualified genomic DNA was stored in 1.0 ml aliquots at −80° C. Aliquots that were subsequently to be used in the amplification assay were stored at 4° C. Each 1 ml aliquot is enough for 8–9 plates or 64 tests.

Gene Amplification Assay:

The ADAM8 was screened in the following primary tumors and the resulting Ct values are reported in Table 5.

TABLE 5

|  | Delta Ct | Fold Increase |
| --- | --- | --- |
| Lung Tumor DNA Panel | | |
| LT 11.1 | 1.12 | 2.17 |
| LT 12.1 | 0.54 | |
| LT 13.1 | 1.43 | 2.69 |
| LT 15.1 | 1.68 | 3.2 |
| LT 16.2 | 0.85 | |
| LT 17.2 | 1.59 | 3.01 |
| LT 18.2 | 1.07 | 2.1 |
| LT 22.1 | −0.17 | |
| Colon Tumor Panel | | |
| 1 | 1.5 | 2.83 |
| 2 | 1.38 | 2.6 |
| 3 | 0.56 | |
| 4 | 1.75 | 3.36 |
| 5 | 2.32 | 4.99 |
| 6 | 1.14 | 2.2 |
| 7 | 0.98 | |
| 8 | 0.91 | |
| 9 | 0.54 | |
| 10 | 1.32 | 2.5 |

TABLE 5-continued

|    | Delta Ct | Fold Increase |
|----|----------|---------------|
| 11 | 2.76     | 6.77          |
| 12 | 1.2      | 2.3           |
| 13 | 0.97     |               |
| 14 | 0.88     |               |
| 16 | 0.88     |               |
| 17 | 0.65     |               |

ADAM8:

The Ct values for a variety of human tumors are reported in Table 5. A Ct of >1 was typically used as the threshold value for amplification scoring, as this represents a doubling of gene copy. Table 5 indicates that significant amplification of ADAM8 occurred in primary lung tumors LT11, LT13, LT15, LT17, and LT18. The average Ct values for these primary lung tumor hits are: 1.12, 1.43, 1.68, 1.59, and 1.07, which represents approximately a 2.17, 2.69, 3.2, 3.01, and 2.1-fold increase, respectively, in gene copy relative to normal tissue. Table 5 also indicates that significant amplification of ADAM8 occurred in primary colon tumors CT1, CT2, CT4, CT5, CT6, CT10, CT11, and CT12. The average Ct values for these primary colon tumor hits are: 1.5, 1.38, 1.75, 2.32, 1.14, 1.32, 2.76, and 1.2, which represents approximately a 2.83, 2.6, 3.36, 4.99, 2.2, 2.5, 6.77, and 2.3-fold increase, respectively, in gene copy relative to normal tissue. Because amplification of ADAM8 occurs in various tumors, it is likely associated with tumor formation and/or growth. As a result, antagonists (eg. antibodies) directed against ADAM8 are useful in cancer therapy.

Example 3

Isolation of cDNA Clones Encoding ADAM8

Total spleen RNA was purchased from Clonetech (#64034-1). Reagents for synthesizing cDNA were purchased from Gibco®BRL (Superscript™ Preamplification System #18089-011). The RNA was used to synthesize oligo dT primed cDNA according to the manufacturer's directions. This cDNA (5 µg) was used in a PCR reaction with ADAM8 specific primers to generate an approximately 880 bp DNA fragment from the 5' end of the ADAM8 mRNA. The specific primers used are as follows:

```
h8-9FBAM forward primer (29 mer)
ATGTGGATCCATGCGCGGCCTCGGGCTCT       (SEQ ID NO:9)

h8-913R reverse primer (21 mer)
CCACAGTAGTCCCGGTGAAGT               (SEQ ID NO:10)
```

The following PCR reaction was set up:
66.43 µl H₂O
10 µl 10× PCR Buffer (PerkinElmer®)
6 µl 25 mM MgCl2 (PerkinElmer®)
8 µl dNTP Mix (PerkinElmer®)
4 µl DMSO
0.5 µl TaqGold (PerkinElmer®)
1.73 µl h8-9FBAM forward primer 1 OD/100 ml
1.34 µl h8-913R reverse primer 1 OD/100 ml
2 µl cDNA (see above)
100 µl total An Ericomp™ TwinBlock thermocycler was used to amplify the ADAM8 fragment according to the following protocol:
initial taq polymerase activation:
95° C. 10 minutes
35 cycles of:
95° C. 15 seconds
53° C. 30 seconds
70° C. 2 minutes
final extension:
72° C. 20 minutes This PCR amplified fragment was cleaned with the Concert™ PCR purification kit (Gibco® BRL), digested with restriction enzymes BamHI and SalI (New England Biolabs) according to the manufacturer's instructions and the 880 bp fragment isolated on a 1% Agarose gel (FMC Corporation). A BamHI site was created in the forward PCR primer while a SalI site occurs in the ADAM8 cDNA sequence. The resulting fragment was cleaned using the Concert™ Gel Purification Kit (Gibco®BRL Corporation). This fragment was ligated (New England Biolabs ligase) into an expression vector called pRK5tkneo, also digested at BamHI and SalI sites in the multiple cloning site and purified in similar fashion as described above. Transformation was done with Stratagene Supercompetent XL1 Blue according to manufacturer's directions. The resulting colonies were grown in 5 ml cultures overnight and small preparations of DNA were made with a Qiagen® miniprep kit. A variety of restriction digests, based on the published sequence, were done to confirm the clone. One was selected for large scale DNA preparation using the Concert™ DNA preparation system (Gibco®BRL).

Cloning Full-length ADAM8 cDNA

A full-length ADAM8 clone was obtained from total UCLAP3 cell line RNA. RNA was made from UCLAP3 cells grown in culture, pelleted, washed with PBS and pelleted again using a commercial kit and treating with DNase (Qiagen® RNeasy® kit). Specifically primed cDNA was made utilizing an RT-PCR kit (Gibco®BRL Thermoscript™ RT-PCR System 11146-016) and an oligonucleotide specific for ADAM8 mRNA. The primer used, referred to as h8-3109R, has the sequence:
5' AGCTGACTCTCCCACATAGCCC 3' (SEQ ID NO: 11).

The cDNA was made according to manufacturer's directions using approximately 5 g of total RNA and an incubation temperature for the reverse transcriptase of 602 C. PCR reactions were performed with Platinum® Taq DNA Polymerase High Fidelity enzyme (Gibco®BRL) using a final concentration of 2 mM MgSO₄. The reverse primer was the same as that listed above for the cDNA reaction and the forward primer, referred to as h8-9Fbam, has the sequence:
5' ATGTGGACCATGCGCGGCCTCGGGCTCT 3'. (SEQ ID NO: 9)

PCR amplification cycling parameters were as follows: 95° C. for 2 minutes as an initial denaturation step; 95° C. for 30 seconds 55° C. for 30 seconds 68° C. for 3 minutes for 40 cycles; 4° C. soak to hold reactions until retrieved. The expected size of the PCR band was approximately 3100 bp and this was confirmed by gel electrophoresis.

The PCR reaction was digested with BamHI and HindIII restriction enzymes and the resulting mixture separated by agarose gel electrophoresis. A band of approximately 3100 bp was extracted from the gel and ligated into a plasmid vector similarly digested with BamHI and HindIII. The resulting clones were sequenced and found to contain several sequence differences relative to the published sequence for ADAM8. These clones may represent ADAM8 variants. Two of these resulted in amino acid changes, Arg to Gly at amino acid number 171 and Lys to Arg at amino acid number 223. They were restored to the publised sequence by digesting out a 346 bp SanDI/SalI fragment and replacing it with a similar fragment from the 880 bp 5' end ADAM8 clone, which contained the published sequence at these loci, using standard molecular biology methods. Two other differences were found in both the full-length clone and the 880 bp 5' end clone: 1) nucleotide number 249 (as measured in GenBank sequence D26579) was found to be a C rather than a T encoding a Gly for amino acid 64 as in the published sequence, and 2) nucleotide number 327 was found to be a C rather than an A encoding a Phe rather than a Leu for amino acid at position 90. In addition, in the full-length clone only, nucleotide number 1263 was found to be a C rather than a T encoding an Arg at amino acid position 402 as in the published sequence. Also, the initiation codon, ATG, was found instead to have the sequence AGA in the full-length clone. Sequencing was done with commercially available kits utilizing fluorescently labeled nucleotides (Big Dye Terminator Cycle Sequencing Kit, PE Applied Biosystems).

Example 4

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169–176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer
1.0 µl DTT (100 mM)
2.0 µl NTP mix (2.5 mM: 10 µl; each of 10 mM GTP, CTP & ATP+10 µl H$_2$O)
1.0 µl UTP (50 µM)
1.0 µl Rnasin
1.0 µl DNA template (1 µg)
1.0 µl H$_2$O
1.0 µl RNA polymerase (for PCR products T3=AS, T7=S, usually)

The tubes were incubated at 37° C. for one hour. 1.0 µl RQ1 DNase was added followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1–3 µl of the probe or 5 µl of RNA Mrk III were added to 3 µl of loading buffer. After heating on a 37° C. heat block for three minutes, the probes were immediately placed on ice. The wells of gel were flushed, the samples loaded, and run at 180–250 volts for 45 minutes. The gel was wrapped in saran wrap and exposed to XAR film with an intensifying screen in −70° C. freezer one hour to overnight.

$^{33}$P-Hybridization

Pretreatment of paraffin-embedded sections: The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes). Slides were subsequently rinsed in 0.5×SSC, dehydrated through graded ethanols and air-dryed.

Prehybridization: The slides were laid out in plastic box lined with Box buffer (4×SSC, 50% formamide)—saturated filter paper. The tissue was covered with 50 µl of hybridization buffer (10% Dextran Sulfate, 50% formamide, 1×SSC) and incubated at 42° C. for 1–4 hours.

Hybridization: 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

Washes: Washing was done 2×10 minutes with 2×SSC, EDTA at room temperature (400 ml 20×SSC+16 ml 0.25 M EDTA, V$_f$=4L), followed by Rnase. A treatment at 37° C. for 30 minutes (500 µl of 10 mg/ml in 250 ml Rnase buffer=20 µg/ml). The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4L).

The following are the primers used to amplify a portion of the ADAM8 sequence contained within the pRK5tkneo vector for use as a probe for in situ hybridization.

upper (T7 promoter+ADAM8):
GGA TTC TAA TAC GAC TCA CTA TAG GGC GAC TCA GCC GCC AGC CTC AGC (SEQ ID NO:12)

lower (T3 promoter+ADAM8):
CTA TGA AAT TAA CCC TCA CTA AAG GGA GCC GCC GTG TCC GTT GC (SEQ ID NO: 13)

The probe was amplified using the Advantage cDNA polymerase mix from Clonetech (8417-1) according to the manufacturer's directions. Cycle conditions were as follows:
10 cycles of:
94° C. 30 seconds
68° C. 30 seconds
72° C. 1 minutes
15 cycles of:
94° C. 30 seconds
55° C. 30 seconds
72° C. 1 minutes
followed by:
72° C. 7 minutes
4° C. hold ADAM 8 in Tissues ADAM 8 was found in the malignant epithelium of lung squamous cell carcinomas, in lung adenocarcinomas, in colon carcinomas, in prostate carcinomas, in breast carcinomas and in inflammatory tissues, etc. Expression was present in malignant cells and in some tumors was present in the stroma immediately adjacent to the tumor. There was some weak patchy expression in various normal tissues.

Normal Tissues:
1. Normal colon (n=2): patchy weak to low level expression in the lamina propria and in mucosal lymphoid follicles.
2. Fetal human skin, epidermis: weak positive expression.
3. Fetal human thymus: low level diffuse expression in thymic medulla.

Normal Human Tissues Microarray (H2000-2 (14-1)):
Adrenal cortex (H97-621 and H99-346): Positive expression in adrenal epithelial cortical epithelial cells. (On a Clinomic array normal adrenal cortex was negative to weak positive)
Lung (H97-621): Negative
Placenta (H97-621): Positive expression in chorionic villi.
Cerebellum (H97-619): Negative
Cerebral cortex (H97-619): Negative
Brainstem (H97-621): Negative
Eye: (HP000971 and 972): Negative
Colon mucosa (P9600313A and H97-621 and H97-254): Negative
Liver, Hepatocytes (H97-621): Negative
Renal Cortex (H97-621): Negative
Ovary (HP001216): Low to weak positive expression in stroma.
Prostate (H97-621: Negative
Lymph node (H97-621 and HP001373): weak positive expression:
Spleen (H97-621 and HP-001249): Positive expression in red pulp; diffuse (white pulp not present in section for evaluation)
Tonsil (H99-346 and HPP001366): weak expression
Skin, dermis (H97-528): Negative
Breast, ducts (H97-528): Negative Adult Multi Tissue Block (KH97-06 6), KH97-04, Misc 02)
1. Low level diffuse expression in the red pulp of the spleen.
2. Lung with subacute suppurative bronchitis: low level specific expression in neutrophils in the suppurative infiltrate in the affected large airways.
3. Pancreas: random pattern of aggregates of silver grains.
4. Tissues that were negative include prostate, liver, pancreas, normal lung (2 sections), placenta, bile duct, and kidney.

Neoplasms:

Lung Squamous Cell CA (n=17) Tumors
1. Negative.
2. Negative:
3. Weak positive expression in patchy areas of the reactive fibrous connective tissue adjacent to some areas of malignant tumor.
4. Weak positive expression in patchy areas of the reactive fibrous connective tissue adjacent to some areas of malignant tumor and weak positive expression in some areas of the malignant tumor.
5. Patchy weak expression in malignant tumor cells (94/15524 E1).
6. There are high background and no apparent consistent signal; in areas with low background there is no signal, in areas with background there is diffuse low signal (5552/96).
7. There is expression in neoplastic cells and in the adjacent stroma; not all areas have expression; this tumor appears to have both SCC and adeno components (5156A1).
8. Negative (2272A2).
9. No significant expression in the SCC or in any other components of this specimen (26A3).
10. SCC present in a large airway. Weak to +1 expression in the focus of squamous cell carcinoma;
+2 diffuse expression in the cortex of a regional (hilar) lymph node with reactive hyperplasia and secondary follicle formation (2641A4).
+1 in a mixed lympho-granulocytic inflammatory infiltrate in the submucosa of the affected large airway.
11. No significant expression in the SCC or in any other components of this specimen (4727A4/98).
12. This squamous cell carcinoma has areas of necrosis and fibroplasia and adjacent non-neoplastic lung; there is no significant expression (98/14964).
13. This squamous cell/adeno-squamous cell carcinoma and adjacent non-neoplastic lung has no significant expression (98/8946).
14. There is positive patchy low level expression in the tumor. In one bronchi with suppurative inflammation (bronchitis), there is patchy expression in the non-neoplastic normal/hyperplastic mucosal epithelium (11046).
15. No significant expression (7915/98).
16. No significant expression (98/15715).
17. No significant expression (98/9210).

Lung Adenocarcinomas (AdCA; n=17)
1. Low level diffuse expression in malignant epithelium. (2484A4/98)
2. Weak to low level diffuse expression in malignant epithelium (96/7468 1)
3. Weak to low level patchy expression in malignant epithelium and adjacent fibrous stroma. (191D2)
4. Moderate diffuse expression in malignant epithelium (94/1585 1B).
5. Negative (95/5590)
6. Low level patchy expression in malignant epithelium (2943A3/98)
7. Negative (526A4)
8. Positive low level diffuse expression in malignant epithelium (95/10302 1B)
9. There is positive significant expression in the neoplastic epithelium of this adenocarcinoma. There is not enough normal lung present in the section to evaluate the level of expression in normal bronchi. The sense probe is negative (H97-618.1B).
10. There is no significant expression (3284A4/98).
11. Though there is patchy moderate expression in some neoplastic epithelial cell clusters, neoplastic cells are predominantly negative. There is also patchy mild expression in some areas of fibroplasia adjacent to the tumor. Areas of inflammation (neutrophilic, lympho-histiocytic) present adjacent to the tumor and regional lymphoid follicles (MALT) are negative (8014/98).
12. There is significant positive, but patchy expression in neoplastic epithelium in this adenocarcinoma. Expression is not present in normal lung epithelium and is minimal in the fibrous stroma of the tumor; expression is predominantly limited to neoplastic epithelium. Not all of the tumor has expression as detected by ISH (14366).

13. Lymph node, the adenocarcinoma has metastasis. This is a metastasis present with a regional lymph node; neither the tumor nor the lymph node has significant expression (10509).
14. There is significant (moderate to strong level) expression in neoplastic epithelium in this adenocarinoma. Expression is not present in normal lung epithelium and is minimal in the fibrous stroma of the tumor; expression is predominantly limited to neoplastic epithelium (95/2527).
15. There is no consistent expression in neoplastic cells; patchy low level expression is present in a few foci with necrosis and degradation. There is moderate expression in some areas of fobroplasia in fibroblasts and there is moderate expression in chondrocytes present in the cartilage rings supporting a large airway. ISH signal in cartilage can sometimes be artifactual (non-specific sticking of probe to hyaline matrix); however here expression overlies cells bodies and nuclei of individual chondrocytes (98/10720).
16. There is significant positive (moderate level) but patchy expression in neoplastic epithelium in this adenocarcinoma. Expression is not present in normal lung epithelium and is minimal in the fibrous stroma of the tumor; expression is predominantly limited to neoplastic epithelium (1072).
17. There is no significant expression (98/15029).

Lung Tumor Multi Block: H1999-637 1: 9 Punch Sections
1. HP001217: carcinoma: strong positive expression in neoplastic cells.
2. HP001261: carcinoma: moderate positive expression in neoplastic cells; low level expression in some fibrous stroma tissue.
3. HP001263: AdCA: moderate positive expression in neoplastic cells.
4. HP001218: AdCA: moderate positive expression in neoplastic cells; no expression in normal bronchial epithelium.
5. HP001233: diffuse low level expression; expression (low) in normal bronchial epithelium.
6. H97-618.2D: AdCA: moderate positive expression in neoplastic cells.
7. H97-618.1D diffuse low level expression.
8. H97-618.1C: carcinoma: moderate expression in neoplastic cells.
9. HP001297: normal: diffuse weak expression in alveoli and bronchial mucosa.

Non-small Cell Lung Carcinoma. SCC: 2 of 8 Specimens had Positive Expression; Adenocarcinoma and Large Cell Carcinoma: 11 of 17 Specimens had Expression
1. poorly differentiated adenocarcinoma: negative
2. mixed adenosquamous carcinoma weak expression
3. adenocarcinoma: weak expression
4. poorly differentiated squamous cell carinoma: negative
5. large cell undifferentiated: positive low expression
6. adenocarcinoma: positive low expression
7. adenocarcinoma: positive low expression
8. epidermoid carcinoma: positive low expression
9. adenocarinoma: weak expression
10. squamous cell carcinoma weak expression
11. adenocarcinoma: weak expression
12. squamous cell carcinoma: negative
13. adenocarcinoma: positive low expression
14. squamous cell carcinoma: positive low expression
15. adenocarcinoma: positive expression
16. adenocarcinoma: positive expression
17. broncho-alveolar carcinoma: positive expression
18. adenocarcinoma: positive expression
19. adenocarcinoma: positive expression
20. adenocarcinoma: weak expression
21. adenocarcinoma: positive expression
22. squamous cell carcinoma: negative
23. squamous cell carcinoma: negative
24. squamous cell carcinoma: negative
25. adenocarcinoma: positive expression
26. squamous cell carcinoma: positive low expression
27. adenocarcinoma: positive expression Small Cell Lung Carcinoma (4 of 8 Specimens had Expression)
1. squamous cell carcinoma: negative
2. Small cell Carcinoma: negative
3. Small cell Carcinoma (inflamed): positive low expression
4. Small cell Carcinoma: negative
5. squamous cell carcinoma (inflamed): positive low expression
6. Small cell Carcinoma: weak expression
7. squamous cell carcinoma: positive low expression
8. squamous cell carcinoma: positive low expression Lung Carcinoma In situ
1. weak expression
2. weak expression
3. weak expression
4. weak expression
5. weak expression Metastatic Lung Tumors
1. large cell carcinoma: weak expression
2. squamous cell carcinoma: weak expression
3. squamous cell carcinoma: weak expression
4. adenocarcinoma weak expression
5. adenocarcinoma: positive low expression
6. squamous cell carcinoma: negative
7. squamous cell carcinoma: weak expression
8. adenocarcinoma: positive low expression
9. adenocarcinoma: weak expression
10. adenocarcinoma: positive low expression
11. adenocarcinoma: positive low expression
12. adenocarcinoma: positive low expression Lung with Eosinophilic Bronchitis (Asthma) (n=2)
1. HP001191 1A IF984: Bronchi with chronic eosinophilic inflammation (asthma): This section contains a large airway with associated BALT and 2 hilar lymph nodes; the airway has severe eosinophilic inflammation in the submucosa. There is +1 to +2 expression in eosinophils, +1 to +2 expression in the cortex of the lymph nodes and within the BALT in the submucosa.
2. HP001192 1C IF984: Lung with asthma, eosinophilic bronchitis. There is specific expression in infiltrating eosinophils and in lymphoid aggregates in BALT and in areas of periarterial lymphocytic inflammation.

Colon Carcinomas (n=10)
1. negative (9729/98 F)
2. negative (7560/98 S)
3. negative (7380/91)
4. negative (9490/98 H)
5. negative (7470/98 C)
6. negative (7698/98 9)
7. negative (7151/98)
8. negative (7306/98 C3)

9. patchy weak positive in the inflamed stroma adjacent to the malignant tumor; no expression in the neoplastic cells. (9153/98 C).
10. low level positive expression in malignant epithelial cells (6561/91).

Colon Tumor Multi Block N1999-636 1 (3 Punch Sections)
1. HP001277: AdCA: There is specific moderate expression in the neoplastic colonic mucosal cells; none to very weak expression in normal colonic mucosa. There is however moderate distinct expression in the lamina propria in leukocytes, specifically in globular leukocytes/eosinophils and some lymphocytes and fibroblasts.
2. HP001232: AdCA: expression is predominantly in leukocytes within the lamina propria; only a few neoplastic mucosal cells have expression.
3. HP001223: AdCA: There is no expression in tumor cells; patchy expression is present in the lamina propria in leukocytes and fibroblasts.
4. HP001209: AdCA: low expression in tumor cells and in the lamina propria.
5. HP001210: AdCA: patchy low to moderate expression in tumor cells.
6. HP001243: AdCA: low expression in tumor cells.

Breast Carcinomas (n=11)
1. Positive low level diffuse expression in malignant epithelium (IF97-015371 E; H97-528).
2. Positive low level expression in the stroma immediately adjacent to the invasive edge of the malignant tumor; no expression in the neoplastic cells in solid nodules/cords. (IF96-283031 B, H97-528).
3. Negative (IF97-128551 C, H97-528).
4. There is low level specific expression in mammary glands; the glands have single to multilayered epithelium; the surrounding tissue is dense collagen (2340/98).
5. There is specific expression in the solid cords/glands of this adenocarcinoma (4202A2).
6. There is expression in the overlying skin epidermal epithelium (diffuse). There was expression in inflamed tumor stroma and in some neoplastic of some tumor foci. The latter was low level and was not consistent throughout the tumor. (5156A1).
7. There is specific expression in tumor cells in this adenocarcinoma. There is also expression in some areas of inflamed stroma adjacent to the malignant foci. Normal glands present comparatively have no or rare expression (13327/97).
8. Breast lobular Carcinoma. No expression (5159B1 H).
9. Breast ductal carcinoma. Low level diffuse expression in the neoplastic cells; in a few areas the stromal elements (fibroblasts) immediately adjacent to the tumor had patchy low level expression (88A).
10. Breast adenocarcinoma. No expression (there are multifocal small aggregates of silver grains present in a random pattern; interpreted as artifact) (9183/97).
11. Breast adenocarcinoma. No expression (3885B1).

Inflammatory Tissue Microarray H2000-29 (4) Clinomics Microarray)

Rheumatoid Arthritis Synovium:
  radial styloid process: Positive expression in synovium
  knee: Positive expression in subsynovial vessels; samples have no synovium to evaluate
  knee: Positive expression in synovium Renal Biopsies with Systemic Lupus Erythematosis
  1. weak Positive expression in the interstitium in areas of inflammation.

Normal Kidney
  1 weak positive expression in tubular epithelium
  2 Negative
  3 weak Positive expression in tubular epithelium Thyroiditis
  Hashimoto s thyroiditis: Negative
  Chronic lymphocytic thyroiditis: Negative
  Chronic lymphocytic thyroiditis: weak positive expression in areas in inflammation
  Chronic lymphocytic thyroiditis: Positive
  Hashimoto's thyroiditis: weak positive expression in areas in inflammation
  Hashimoto's thyroiditis: Negative
  Focal autoimmune thyroiditis: Negative
  Hashimoto's thyroiditis: Negative
  Chronic thyroiditis with Hurthle cell metaplasia Normal Thyroid
  1 weak positive expression in epithelium
  2 Negative (n=3)

Normal Pancreas
  1 Negative (n=4)

Psoriasis
  1 Positive expression in psoriatic epidermis (n=4)

Chronic Dermatitis
  1. Licehnoid chronic dermatitis with dermatophytosis: Positive low level expression in the dermis
  2. A typical lymphocytic dermatitis, Mycosis fungoides: Positive moderate expression in the affected dermis Normal Skin
  1 Positive low level expression in epidermis (n=2)

Asthma: lung
  Fibrosing alveolitis with asthma: weak expression in affected alveolar interstitium (n=3)
  Pulmonary atelectasis with asthma: Negative (n=3)
  Asthma: Negative (n=2)

Chronic Obstructive Pulmonary Disease
  Extrinsic allergic alveolitis, COPD: weak expression in affected alveolar interstitium
  COPD and congestion: weak expression in affected alveolar interstitium
  Acute and chronic congestion and COPD: Negative
  COPD: weak expression in inflamed interstitium
  Acute and chronic pleuritis, COPD: weak expression in affected alveolar interstitium
  COPD: Positive moderate expression in inflamed fibrous tissue
  COPD, pleuritis and empyema: Positive moderate expression in inflamed fibrous tissue Bacterial Pneumonia
  1. focal lipoid pneumonia: Positive low expression in inflamed interstitium an possibly in alveoli
  2. obstructive pneumonia and COPD: Positive moderate expression in inflamed interstitium an possibly in alveoli
  3. pneumonia, organizing: Negative
  4. bronchopneumonia with lymphoid aggregates: Positive low expression in inflamed interstitium an possibly in alveoli 5. acute bronchopneumonia: Positive low expression in inflamed interstitium
6. aspiration pneumonia with *S. aureus:* Positive moderate expression in inflamed interstitium Normal Lung
Negative (n=8)

Tuberculosis
chronic interstitial inflammation: Positive moderate expression in inflamed interstitium (n=2)

Tonsils
1. 95-8950: No expression.
2. H1999-663 8-3 1372: +1 to +2 expression in tonsil crypt epithelium cells (epithelial cells and or infiltrating. mononuclear cells); +1 expression in discrete cells in germinal centers which are most likely dendritic cells, diffusely in mononuclear cells in marginal zone and paracortex areas of tonsil. There is low level (0 to +1) expression in the overlying oral mucosa epithelium.
3. H1999-663 6-3 1370: +2 expression in tonsil crypt epithelium cells (epithelial cells and or infiltrating mononuclear cells); +1 expression in discrete cells in germinal centers which are most likely dendritic cells, +1 expression diffusely in mononuclear cells (monocytes) in mantle zone and paracortex areas of tonsil. There is low level (+1) expression in the overlying oral mucosa epithelium.
4. H1999-663 7-3 1371: +2 expression in tonsil crypt epithelium cells (epithelial cells and some infiltrating mononuclear cells); +1 expression cells in germinal centers and in discrete cells which are most likely dendritic cells, +1 expression diffusely in mononuclear cells (monocytes) in mantle zone and paracortex areas of tonsil. There is low level (+1) expression in the overlying oral mucosa epithelium.
5. H1999-663 5-3 1369: +2 expression in tonsil crypt epithelium cells (epithelial cells and some infiltrating mononuclear cells); +1 expression cells in germinal centers and in discrete cells which are most likely dendritic cells, +1 expression diffusely in mononuclear cells (monocytes) in marginal zone and paracortex areas of tonsil.

Spleen
1. H1999-663 12-3 1376: high background precludes assessment for expression; there is no specific expression over this background.
2. H1999-663 14-4 1378: +1 diffuse expression in red pulp; +1 expression in mononuclear cells in peri-arterial lymphoid sheaths (PALS) and in the marginal zone of primary or secondary follicles.
3. H1999-663 10-3 1374: No significant signal.
4. H1999-663 13-4 1377: No significant signal.
5. H1999-663 18-3 1382: +1 diffuse expression in red pulp; +1 to +2 expression in mononuclear cells in peri-arterial lymphoid sheaths (PALS) and in the marginal zone of primary or secondary follicles; +1 expression in germinal centers of follicles of secondary follicles.
6. H11999-663 11-3 1375: +1 diffuse expression in red pulp; +1 expression in mononuclear cells in peri-arterial lymphoid sheaths (PALS) and in the marginal zone of primary or secondary follicles; +1 expression in germinal centers of follicles of secondary follicles.
7. H1999-663 17-3 1381: +1 diffuse expression in red pulp; +1 expression in mononuclear cells in peri-arterial lymphoid sheaths (PALS) and in the marginal zone of primary or secondary follicles; +1 expression in germinal centers of follicles of secondary follicles.
8. H1999-663 19-3 1383: Weak to +1 diffuse expression in red pulp; +1 expression in mononuclear cells in peri-arterial lymphoid sheaths (PALS) and in the marginal zone of primary or secondary follicles; +1 expression in germinal centers of follicles of secondary follicles.
9. H1999-663 15-4 1379: Weak to +1 diffuse expression in red pulp; +1 expression in mononuclear cells peri-arterial lymphoid sheaths (PALS) and in the marginal zone of primary or secondary follicles; +1 expression in germinal centers of follicles of secondary follicles.

Prostate Tumor Array (H2000-26 (4); Clinomics):

Normal Prostate
CL1999-1: no mucosa is present: Negative
CL 1999-2: no mucosa is present: Negative
CL 1999-3: Low Positive expression in prostate mucosal epithelium
CL 1999-4: Low Positive expression in prostate mucosal epithelium Benign Hyperplasia
CL 1999-6: Positive expression in prostate mucosal epithelium; weak positive signal in underlying fibrous stroma.
CL 1999-7: Positive expression in prostate mucosal epithelium; weak positive signal in underlying fibrous stroma.
CL 1999-10: Positive expression in prostate mucosal epithelium PIN: Low Grade:
CL 1999-11: Positive expression in prostate mucosal epithelium
CL 1999-12: Positive expression in prostate mucosal epithelium
CL 1999-13: Positive expression in prostate mucosal epithelium
CL 1999-14: Positive expression in prostate mucosal epithelium
CL 1999-15: Positive expression in prostate mucosal epithelium PIN High Grade:
CL 1999-16: Negative
CL 1999-18: Positive expression in prostate mucosal epithelium
CL-1999-19: Positive expression in prostate mucosal epithelium
CL 1999-20: Positive expression in prostate mucosal epithelium; weak expression in underlying fibrous stroma Prostatic Carcinoma:
CL 1999-21: Positive expression in prostate mucosal epithelium
CL 1999-22 Positive expression in prostate mucosal epithelium
CL 1999-23 Positive expression in prostate mucosal epithelium
CL 1999-24 Positive expression in prostate mucosal epithelium
CL 1999-25 Positive expression in prostate mucosal epithelium
CL 1999-26 Positive expression in prostate mucosal epithelium
CL 1999-27 Positive expression in prostate mucosal epithelium
CL 1999-28 Positive expression in prostate mucosal epithelium CL 1999-29 Positive expression in prostate mucosal epithelium
CL 1999-30 Positive expression in prostate mucosal epithelium
CL 1999-31 Positive expression in prostate mucosal epithelium
CL 1999-32 Positive expression in prostate mucosal epithelium
CL 1999-33 Positive expression in prostate mucosal epithelium
CL 1999-34 Positive expression in prostate mucosal epithelium
CL 1999-35 Positive expression in prostate mucosal epithelium
CL 1999-36 Positive expression in prostate mucosal epithelium
CL 1999-37 Negative
CL 1999-38 Negative
CL 1999-39 Positive expression in prostate mucosal epithelium
CL 1999-40 Weak expression in prostate mucosal epithelium
CL 1999-41 Positive expression in prostate mucosal epithelium
CL 1999-42 Negative
CL 1999-43 Weak expression in prostate mucosal epithelium
CL 1999-44 Negative
CL 1999-45 Positive expression in prostate mucosal epithelium
CL 1999-46 weak expression in prostate mucosal epithelium
CL 1999-48 Weak expression in prostate mucosal epithelium
CL 1999-49 Weak expression in prostate mucosal epithelium
CL 1999-50 Weak expression in prostate mucosal epithelium
CL 1999-51 Positiveexpression in prostate mucosal epithelium
CL 1999-52 Negative
CL 1999-53 Positive expression in prostate mucosal epithelium
CL 1999-54 Weak expression in prostate mucosal epithelium
CL 1999-55 Weak expression in prostate mucosal epithelium
CL 1999-56 Weak expression in prostate mucosal epithelium
CL 1999-57 Weak expression in prostate mucosal epithelium
CL 1999-58 Weak expression in prostate mucosal epithelium
CL 1999-59 Weak expression in prostate mucosal epithelium
CL 1999-60 Positive expression in prostate mucosal epithelium
CL 1999-61 Positive expression in prostate mucosal epithelium
CL 1999-62 Positive expression in prostate mucosal epithelium
CL 1999-63 Positive expression in prostate mucosal epithelium
CL 1999-64 Positive expression in prostate mucosal epithelium
CL 1999-65 Positive expression in prostate mucosal epithelium
CL 1999-66 Positive expression in prostate mucosal epithelium
CL 1999-67 Weak expression in prostate mucosal epithelium
CL 1999-68 Positive expression in prostate mucosal epithelium
CL 1999-69 Positive expression in prostate mucosal epithelium
CL 1999-70 Positive expression in prostate mucosal epithelium
CL 1999-71 Positive expression in prostate mucosal epithelium Prostatic Adenocarcinoma:
CL 1999-73 Positive expression in prostate epithelium
CL 1999-74 Positive expression in prostate epithelium
CL 1999-75 Positive expression in prostate epithelium
CL 1999-76 Positive expression in prostate epithelium
CL 1999-77 Positive expression in prostate epithelium
CL 1999-78 Positive expression in prostate epithelium
CL 1999-79 Positive expression in prostate epithelium
CL 1999-80 Positive expression in prostate epithelium Metastatic Prostatic Cancer:
CL 1999-81 Positive expression in prostate epithelium
CL 1999-82 Positive expression in prostate epithelium
CL 1999-83 Positive expression in prostate epithelium
CL 1999-84 Positive expression in prostate epithelium
CL 1999-85 Positive expression in prostate epithelium
CL 1999-86 Positive expression in prostate epithelium
CL 1999-87 Positive expression in prostate epithelium
CL 1999-88 Positive expression in prostate epithelium
CL 1999-89 Positive expression in prostate epithelium
CL 1999-90 Positive expression in prostate epithelium
CL 1999-91 Positive expression in prostate epithelium
CL 1999-92 Positive expression in prostate epithelium
CL 1999-93 Positive expression in prostate epithelium
CL 1999-94 Positive expression in prostate epithelium
CL 1999-95 Positive expression in prostate epithelium Prostatic Atrophy:
CL 1999-99 Positive expression in prostate mucosal epithelium Thymus
1. H97-084 01: A section of fetal thymus (age not specified); There is specific signal restricted to the thymic cortex. Signal here is within a subset of the cells and appears specific to the medullary thymic epithelial cells as opposed to the lymphocyte component of this region of the thymus. Expression in the cortex is absent (note a different type of reticular epithelial cell exists in the cortex).

Human Fetal Tissue (14.5 wk)
1. H97-106 31: A transverse abdominal section containing: Liver with EMH, bowel, abdominal wall, pancreas, ribs, skeletal muscle, kidneys: No significant expression.

Example 5

Use of ADAM8 as a Hybridization Probe

The following method describes use of a nucleotide sequence encoding an ADAM8 polypeptide as a hybridization probe.

DNA comprising the coding sequence of a full-length or mature ADAM8 polypeptide as disclosed herein and/or fragments thereof may be employed as a probe to screen for homologous DNAs (such as those encoding naturally-occurring variants of ADAM8) in human tissue cDNA libraries or human tissue genomic libraries.

Hybridization and washing of filters containing either library DNAs is performed under the following high stringency conditions. Hybridization of radiolabeled ADAM8-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence ADAM8 can then be identified using standard techniques known in the art.

Example 6

Expression of "ADAM8" Polypeptides in E. coli.

This example illustrates preparation of an unglycosylated form of ADAM8 by recombinant expression in E. coli.

The DNA sequence encoding the ADAM8 polypeptide of interest is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the ADAM8 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized ADAM8 protein can then be purified using a metal chelating column under conditions that allow tight binding of the protein.

ADAM8 can be expressed in E. coli in a poly-His tagged form, using the following procedure. The DNA encoding ADAM8 is initially amplified using selected PCR primers. The primers contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(laclq). Transformants are first grown in LB containing 50 mg/ml carbenicillin at 30 C with shaking until an O.D.600 of 3–5 is reached. Cultures are then diluted 50–100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30 C with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4 C. This step results in a denatured protein with all cysteine residues blocked by sulfitolization. The solution is centrifuged at 40,000 rpm in a Beckman Ultracentifuge for 30 mm. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen® Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4C. Protein concentration is estimated by its absorbance at 280 nm using the calculated extinction coefficient based on its amino acid sequence.

The proteins are refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4 C for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded ADAM8 protein are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

For example, PCR reactions were set up using a full-length ADAM8 clone, which contained 346 bp SanDI to SalI fragment from the 5' end clone of ADAM8, as a template. This construct is described in Example 3. The forward primer, ST239A8MF (42 mer), for this reaction is as follows:
5' CATCAAATGCATCAAGACTCTCTGC-CATCCCGAGAGACCCGC 3' (SEQ ID NO: 14).

The sequence for the reverse primer, ST239A8TCR (54 mer), is as follows:
5' CCGAGCTCGAGCGGCCGCAGTCGATT-AGCTCCCGGACGCTGCGTGCACCTCAGT 3' (SEQ ID NO: 15).

The forward sequence was designed with an NsiI restriction site toward the 5' end followed by the sequence of the beginning of the mature sequence of ADAM8, consisting of the amino acid sequence: DSLPSRETR (SEQ ID NO: 21). The reverse primer sequence was designed with an SstI restriction site near the 5' end followed by a NotI restriction site, a stop codon and the sequence of ADAM8 ending at the beginning of the transmembrane domain: TEVHAASGS (SEQ ID NO: 22). Thus, the ADAM8 sequence inserted into the expression vector constitutes the mature extracellular domain. PCR reactions were set up using Platinum® Taq, HF PCR buffer, and 2 mM $MgSO_4$ final (Gibco®BRL). Reactions were incubated as follows: 95° C. for 2 minutes, then 40 cycles of 95° C. for 30 seconds 55° C. for 30 seconds, and 68° C. for 3 minutes, followed by a soak at 4° C. until the reactions were retrieved. The reaction was purified using Concert™ rapid PCR purification columns (Gibco®BRL) and digested with NsiI and SacI. A vector called pST239 was also digested with NsiI and Sacd. The two fragments were gel purified and ligated together to form the final construct, pST239.ADAM8mat, the sequence of which was verified.

The vector pST239 was derived from pBR322 and contains an N-terminal polyhis leader at the 3' end of which exits an NsiI restriction site. This leader provides for optimal translation initiation, purification on a Ni chelation column, and efficient removal if desired with the TAGZyme system (Unizyme Laboratories, Horsholn Denmark). The amino acid sequence of the leader is the following: MKHQHQHQHQHQHQMHQ (SEQ ID NO: 16). Transcription is controlled by the *E.coli* alkaline phosphastase promoter (Kikuchi Y. et. al., Nucleic Acids Research 9:5671–5678, 1981), and the trp operon ribosome binding site (Yanofsky C. et. al., Nucleic acids Research 9:6647–6668, 1981) provides for translation. Downstream of the translation termination codon is the λto transcriptional terminator (Scholtissek S. et. al., Nucleic Acids Research 15:3185, 1987) followed by the rare codon tRNA genes pro2, argU, and glyT (Komine Y., et. al., J. Mol. Biol. 212:579–598, 1990 and Fournier M. J. et. al., Microbiol. Rev. 49:379–397, 1985).

The plasmid pST239.ADAM8mat was transformed into the *E. coli* strain 58F3 (fhuAΔ(tonAΔ) lonΔ galE rpoHts (htpRts) ΔclpP laclq ΔompTΔ(nmpc-fepE) ΔslyD). A Luria Broth culture of one of the transformants was first grown overnight at 30 degrees C., and then diluted 100-fold into a phosphate limiting media to induce the alkaline phosphatase promoter. After 24 hours at 10 degrees C. with shaking, the cultures were centrifuged, and the cell pastes frozen until the start of purification.

*E. coli* pastes (6–10 gm pellets) were resuspended in 10 volumes (w/v) of 7 M guanidine HCl, 20 mM Tris, pH 8, buffer. Solid sodium sulfite and sodium tetrathionate were added to make final concentrations of 0.1 M and 0.02 M, respectively, and the solution was stirred overnight at 4° C.

The solution was clarified by centrifugation and loaded onto a Qiagen® Ni—NTA metal chelate column equilibrated in 6 M guanidine, HCl, 20 mM Tris, pH 7.4. The column was washed with additional buffer containing 50 mM imidazole (Calbiochem, Utrol grade). The protein was eluted with buffer containing 250 mM imidazole. The eluate was further purified on a Pharmacia S-200 gel filtration column in buffer containing 6 M guanidine, 20 mM MES, pH 6.0. Fractions containing the desired protein were pooled, dialyzed against 2 M urea, 20 mM glycine, 10 mM DTT, 50 mM Tris, pH 7.4 and stored at 4° C.

Example 7

Expression of ADAM8 in Mammalian Cells

This example illustrates preparation of a potentially glycosylated form of ADAM8 by recombinant expression in mammalian cells.

The vector, pRK5 (see EP 307,247, published Mar. 15, 1989), is employed as the expression vector. Optionally, the ADAM8 DNA is ligated into pRK5 with selected restriction enzymes to allow insertion of the ADAM8 DNA using ligation methods such as described in Sambrook et al., supra. The resulting vector is called pRK5-ADAM8. In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-ADAM8 DNA is mixed with about 1 μg DNA encoding the VA RNA gene [Thimmappaya et al., *Cell* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of ADAM8 polypeptide. The cultures containing transfected cells may undergo further incubation (in serum free medium) and the medium is tested in selected bioassays.

In an alternative technique, ADAM8 DNA may be introduced into 293 cells transiently using the dextran sulfate method described by Somparyrac et al., *Proc. Natl. Acad. Sci.* 12:7575 (1981). 293 cells are grown to maximal density in a spinner flask and 700 μg pRK5-ADAM8 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed ADAM8 can then be concentrated and purified by any selected method, such as dialysis and/or column chromatography.

In another embodiment ADAM8 can be expressed in CHO cells. The pRK5-ADAM8 vector can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of ADAM8 polypeptide, the culture medium may be replaced with serum free medium. Preferably, the cultures are incubated for about 6 days, and then the conditioned medium is harvested. The medium containing the expressed ADAM8 can then be concentrated and purified by any selected method.

Epitope-tagged ADAM8 may also be expressed in host CHO cells. The ADAM8 may be subcloned out of the pRK5 vector. The subclone insert can undergo PCR to fuse in frame with a selected epitope tag such as a poly-His tag into a Baculovirus expression vector. The poly-His tagged ADAM8 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged ADAM8 can then be concentrated and purified by any selected method, such as by Ni$^{2+}$ chelate affinity chromatography.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector uses expression in CHO cells is as described in Lucas et al., *Nucl. Acids Res.* 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA are introduced into approximately 10 million CHO cells using commercially available transfection reagents Superfect® (Qiagen®), Dosper® or Fugene® (Boehringer Mannheim). The cells are grown and described in Lucas et al., supra. Approximately $3\times10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 is preferred. 3L production spinner is seeded at $1.2\times10^6$ cells/mL. On day 0, the cell number pH are determined. On day 1, the spinner is sampled and sparging with filtered air is commenced. On day 2, the spinner is sampled and 30 mL of 500 g/L glucose and 0.6 mL of 10% antifoam (e.g., 35% polydimethylsiloxane emulsion, Dow Coming 365 Medical Grade Emulsion) is added. Throughout the production, pH is adjusted as necessary to keep at around 7.2. After 10 days, or until viability dropped below 70%, the cell culture is harvested by centrifugation and filtering through a 0.22 µm filter. The filtrate is either stored at 4° C. or immediately loaded onto columns for purification.

For the poly-His tagged constructs, the proteins are purified using a Ni—NTA column (Qiagen®). Before purification, imidazole is added to the conditioned media to a concentration of 5 mM. The conditioned media is pumped onto a 6 ml Ni—NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 µM imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at –80° C.

Immunoadhesin (Fc containing) constructs are purified from the conditioned media as follows. The conditioned medium is pumped onto a 5 ml Protein A column (Pharmacia) which has been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 .mu.L of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

For example, PCR reactions were set up using a full-length ADAM8 clone, which contained 346 bp SanDI to SalI fragment from the 5' end clone of ADAM8, as a template. This construct is described in Example 3. The forward primer, PRKA8F, for this reaction is as follows:

5' GCTGCATGAATTCATGCGCGGC-CTCGGGCTCTGGCTGCTGGGC 3' (43 mer) (SEQ ID NO: 17)

The sequence of the reverse primer, PRKA8R, is as follows:

5' GAGTTTTGTCGGTGACCGACCCG-GACGCTGCGTGCACCTCAGTCAG 3' (46 mer) (SEQ ID NO: 18).

The forward sequence was designed with an EcoRI restriction site toward the 5' end followed by the sequence of the beginning of the signal sequence of ADAM8, consisting of the amino acid sequence: MRGLGLWLLG (SEQ ID NO: 19). The reverse primer sequence was designed with an BstEII restriction site near the 5' end followed by the sequence of ADAM8 ending at the beginning of the transmembrane domain: LTEVHAASGS (SEQ ID NO: 20). Thus, the ADAM8 sequence inserted into the expression vector constitutes the extracellular domain, including the signal sequence, pro domain, metalloproteinase domain, disintegrin domain, cystine rich domain, and the EGF domain. PCR reactions were set up using Platinum® Taq, HF PCR buffer, and 2 mM MgSO$_4$ final (Gibco®BRL). Reactions were incubated as follows: 95° C. for 2 minutes, then 40 cycles of 95° C. for 30 seconds, 55° C. for 30 seconds, and 68° C. for 3 minutes, followed by a soak at 4° C. until the reactions were retrieved. The reaction was purified using Concert® rapid PCR purification columns (Gibco®BRL) and digested with EcoRI and BstEII. A pRK5 vector containing the Fc portion of a human IgG1 designed with a BstEII restriction site such that ligation of an extracellular domain into this restriction site forms a fusion with the human IgG1 Fe, was also digested with BstEII and EcoRI. The two fragments were gel purified and ligated together to form the final construct, pRK.ADAM8Ig, the sequence of which was verified.

This plasmid, containing the extracellular domain of human ADAM8 fused to a human IgG1Fc, was transfected into 293 cells (Graham, F. L. et. al., J. Gen. Virol. 36, 59–74, 1977) using a calcium phosphate method (Gorman, C. et. al., Science 221, 551–553, 1983) and 10 ug of plasmid along with 1 ug of a plasmid containing a gene that confers Neomycin resistance. These cells were selected with 800 ug/ml of Geneticin (Gibco®BRL) and grown in 50:50 F112:DMEM media supplemented with 1× L-Glutamine (Gibco®BRL) and 10% FBS. These cells were used in assays described in Example 10.

Recombinant protein production was performed using a Chinese hamster ovary (CHO) cell line designated DP12-DHFR+ (EP 307,247 published 15 Mar. 1989). These cells were derived from a dihydrofolate minus (dhfr−) DUKX CHO host (Urlaub and Chasin, Proc. Natl. Acad. Sci. USA, 77:4216 [1980]) which were stably transfected with a DHFR+ plasmid to allow for rapid growth in suspension cultures.

The plasmid pADAM8.IgG was introduced into this cell line using the large scale transient transfection method as follows: 1.95 liters of DP12-DHFR+ cells at a density of 1.5×106 cells/ml were seeded in selective growth medium (modified HAM F12/DMEM with trace elements as described in U.S. Pat. No. 5,122,469.) For composition of DMEM and HAM F12 media, see culture formulations in American Type Culture Collection Catalogue of Cell Lines and Hybridomas, Sixth Edition, 1988, pages 346–349. This medium was supplemented with 2 mg/L insulin, 1% fetal bovine serum (Gibco®), and 0.15 g/L gentamycin sulfate. The cells were incubated for one to two hours in this medium before the transfection event.

The transfection complex was generated by mixing 6 mg of plasmid DNA (purified by Qiagen® Gigaprep procedure) with 12 ml of cationic lipid reagent (equivalent to DMRIE-C, Life Technologies, Inc.) in 1.05 liters of complexing media (modified HAMS F12/DMEM, same as above) without additions. The transfection complex was incubated for 30–60 minutes and was then mixed with the cells. The transfected cell culture was divided into three 1L cultures and incubated in 3L spinner vessels at 37° C.

At 24 hours, the transfected cell culture was medium exchanged to remove serum and transfection reagents by centrifuging at 1000 rpm for 8 minutes. Transfected cells were resuspended in production media (modified HAM F12/DMEM with trace elements and Super amino acids as described in U.S. Pat. No. 5,122,469) supplemented with 2 mg/L insulin, 0.15 g/L gentamycin sulfate, 30 g/L glucose and 125 ml/L 20% primatone P3 (Quest). The cell culture was placed at 33° C. for the remainder of the production period. pH was controlled through additions of $Na_2CO_3$. The culture was harvested on day 7 and the recombinant protein product was purified by Protein A (ProSep) chromatography.

To 3.5 liters of conditioned media was added 1 mM sodium azide and 1 mM PMSF which was then loaded over a 6 ml Prosep A (protein A) column overnight at 4C. The column was washed with PBS to baseline O.D., washed with 0.5M TMAC in PBS, washed with PBS and eluted with 50 mM sodium citrate pH3.0 and immediately neutralized with ⅕ volume of 1 M Hepes pH 7.2. The material was then dialyzed into PBS overnight, sterile filtered and stored at 4 C. Yield 32 ml×0.47 mg/ml=15 mg.

After purification the SDS gel revealed disulfide aggregation. Disulfide aggregation is known to occur with some Fc constructs. Baculovirus or CHO His (c-terminal) tag or CHO Flag (n-terminal) tag versions can be prepared using the methods generally discribed above to provide less aggregated material.

Example 8

Expression of ADAM8 in Yeast

The following method describes recombinant expression of ADAM8 in yeast.

First, yeast expression vectors are constructed for intracellular production or secretion of ADAM8 from the ADH2/GAPDH promoter. DNA encoding ADAM8 and the promoter is inserted into suitable restriction enzyme sites in the selected plasmid to direct intracellular expression of ADAM8. For secretion, DNA encoding ADAM8 can be cloned into the selected plasmid, together with DNA encoding the ADH2/GAPDH promoter, a native ADAM8 signal peptide or other mammalian signal peptide, or, for example, a yeast alpha-factor or invertase secretory signal/leader sequence, and linker sequences (if needed) for expression of ADAM8.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant ADAM8 can subsequently be isolated and purified by removing the yeast cells from the fermentation medium by centrifugation and then concentrating the medium using selected cartridge filters. The concentrate containing ADAM8 may further be purified using selected column chromatography resins.

Example 9

Expression of ADAM8 in Baculovirus-infected Insect Cells

The following method describes recombinant expression in Baculovirus-infected insect cells.

The sequence coding for ADAM8 is fused upstream of an epitope tag contained within a baculovirus expression vector. Such epitope tags include poly-His tags and immunoglobulin tags (like Fc regions of IgG). A variety of plasmids may be employed, including plasmids derived from commercially available plasmids such as pVL1393 (Novagen). Briefly, the sequence encoding ADAM8 or the desired portion of the coding sequence of ADAM8 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("SF9") cells (ATCC CRL 1711) using Lipofectin® (commercially available from Gibco®-BRL). After 4–5 days of incubation at 28° C., the released viruses are harvested and used for further amplifications. Viral infection and protein expression are performed as described by O'Reilley et al., *Baculovirus expression vectors: A Laboratory Manual,* Oxford: Oxford University Press (1994).

Expressed poly-His tagged ADAM8 can then be purified, for example, by $Ni^{2+}$-chelate affinity chromatography as follows. Extracts are prepared from recombinant virus-infected Sf9 cells as described by Rupert et al., Nature 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 mm filter. A $Ni^{2+}$-NTA agarose column (commercially available from Qiagen®) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen®). Fractions containing the eluted $His_{10}$-tagged ADAM8, respectively, are pooled and dialyzed against loading buffer.

Alternatively, purification of the IgG tagged (or Fc tagged) ADAM8 can be performed using known chromatography techniques, including for instance, Protein A or protein G column chromatography.

Following PCR amplification, the respective coding sequences are subcloned into a baculovirus expression vector (pb.PH.IgG for IgG fusions and pb.PH.His.c for poly-His tagged proteins), and the vector and Baculogold® baculovirus DNA (Pharmingen) are co-transfected into $10^5$ Spodoptera frugiperda ("Sf9") cells (ATCC CRL 1711), using Lipofectin® (Gibco® BRL). pb.PH.IgG and pb.PH.His are modifications of the commercially available baculovirus expression vector pYL1393 (Pharmingen), with modified polylinker regions to include the His or Fc tag sequences. The cells are grown in Hinks TNM-FH medium supplemented with 10% FBS (Hyclone). Cells are incubated for 5 days at 28° C. The supernatant is harvested and subsequently used for the first viral amplification by infecting Sf9 cells in Hinks TNM-FH medium supplemented with 10% FBS at an approximate multiplicity of infection (MOI) of 10. Cells are incubated for 3 days at 28° C. The supernatant is harvested and the expression of the constructs in the baculovirus expression vector is determined by batch binding of 1 ml of supernatant to 25 mL of Ni—NTA beads (Qiagen®) for histidine tagged proteins or Protein-A Sepharose® CL-4B beads (Pharmacia) for IgG tagged proteins followed by SDS-PAGE analysis comparing to a known concentration of protein standard by Coomassie blue staining.

The first viral amplification supernatant is used to infect a spinner culture (500 ml) of Sf9 cells grown in ESF-921 medium (Expression Systems LLC) at an approximate MOI of 0.1. Cells are incubated for 3 days at 28 C. The supernatant is harvested and filtered. Batch binding and SDS-PAGE analysis is repeated, as necessary, until expression of the spinner culture is confirmed.

The conditioned medium from the transfected cells (0.5 to 3 L) is harvested by centrifugation to remove the cells and filtered through 0.22 micron filters. For poly-His tagged constructs, the protein construct is purified using a Ni—NTA column (Qiagen®). Before purification, imidazole is added to the conditioned media to a concentration of 5 mM. The conditioned media are pumped onto a 6 ml Ni—NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of proteins are purified from the conditioned media as follows. The conditioned media are pumped onto a 5 ml Protein A column (Pharmacia) which has been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 mL of 1 M Tris buffer, pH 9. The highly purified protein is subsequently desalted into storage buffer as described above for the poly-His tagged proteins. The homogeneity of the proteins is verified by SDS polyacrylamide gel (PEG) electrophoresis and N-terminal amino acid sequencing by Edman degradation.

Alternatively, a modified baculovirus procedure may be used incorporating high 5 cells. In this procedure, the DNA encoding the desired sequence is amplified with suitable systems, such as Pfu (Stratagene), or fused upstream (5'-of) of an epitope tag contained with a baculovirus expression vector. Such epitope tags include poly-his tags and immunoglobulin tags (like Fc regions of IgG). A variety of plasmids may be employed, including plasmids derived from commercially available plasmids such as pIE1-1 (Novagen). The pIE1-1 and pIE1-2 vectors are designed for constitutive expression of recombinant proteins from the baculovirus ie1 promoter in stably-transformed insect cells. The plasmids differ only in the orientation of the multiple cloning sites and contain all promoter sequences known to be important for ie1-mediated gene expression in uninfected insect cells as well as the hr5 enhancer element. pIE1-1 and pIE1-2 include the translation initiation site and can be used to produce fusion proteins. Briefly, the desired sequence or the desired portion of the sequence (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector. For example, derivatives of pIE1-1 can include the Fc region of human IgG (pb-.PH.IgG) or an 8 histidine (pb.PH.His) tag downstream (3'-of) the desired sequence. Preferably, the vector construct is sequenced for confirmation.

Hi5 cells are grown to a confluency of 50% under the conditions of, 27 C, no $CO_2$, NO pen/strep. For each 150 mm plate, 30 ug of pIE based vector containing the sequence is mixed with 1 ml Ex-Cell medium (Media: Ex-Cell 401+ 1/100 L-Glu JRH Biosciences #14401-78P (note: this media is light sensitive)), and in a separate tube, 100 ul of CellFectin® (CellFectin® (Gibco®BRL #10362-010) (vortexed to mix)) is mixed with 1 ml of Ex-Cell medium. The two solutions are combined and allowed to incubate at room temperature for 15 minutes. 8 ml of Ex-Cell media is added to the 2 ml of DNA/CellFectin® mix and this is layered on Hi5 cells that have been washed once with Ex-Cell media. The plate is then incubated in darkness for 1 hour at room temperature. The DNA/CellFectin® mix is then aspirated, and the cells are washed once with Ex-Cell to remove excess CellFectin®. 30 ml of fresh Ex-Cell media is added and the cells are incubated for 3 days at 28° C. The supernatant is harvested and the expression of the sequence in the baculovirus expression vector is determined by batch binding of 1 ml of supernatant to 25 mL of Ni—NTA beads (Qiagen®) for histidine tagged proteins or Protein-A Sepharose® CL-4B beads (Pharmacia) for IgG tagged proteins followed by SDS-PAGE analysis comparing to a known concentration of protein standard by Coomassie blue staining.

The conditioned media from the transfected cells (0.5 to 3 L) is harvested by centrifugation to remove the cells and filtered through 0.22 micron filters. For poly-His tagged constructs, the protein comprising the sequence is purified using a Ni—NTA column (Qiagen®). Before purification, imidazole is added to the conditioned media to a concentration of 5 mM. The conditioned media is pumped onto a 6 ml Ni—NTA column equilibrated in 20 mM Hepes, pH 7.4, buffer containing 0.3 M NaCl and 5 mM imidazole at a flow rate of 4–5 ml/min. at 48° C. After loading, the column is washed with additional equilibration buffer and the protein eluted with equilibration buffer containing 0.25 M imidazole. The highly purified protein is then subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of proteins are purified from the conditioned media as follows. The conditioned media is pumped onto a 5 ml Protein A column (Pharmacia) which has been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 mL of 1 M Tris buffer, pH 9. The highly purified protein is subsequently desalted into storage buffer as described above for poly-His tagged proteins. The homogeneity of the sequence is assessed by SDS polyacrylamide gels and by N-terminal amino acid sequencing by Edman degradation and other analytical procedures as desired or necessary.

Example 10

Preparation of Antibodies that Bind ADAM8

This example illustrates preparation of monoclonal antibodies that can specifically bind ADAM8.

General Description

Techniques for producing the monoclonal antibodies are known in the art and are described, for instance, in Goding, supra. Immunogens that may be employed include purified ADAM8, fusion proteins containing ADAM8 and cells expressing recombinant ADAM8 on the cell surface. The skilled artisan without undue experimentation can make selection of the immunogen. For example, human ADAM8 was produced with an epitope tag (polyHQ) at the N-terminus in E. coli and formulated in 50 mM Tris containing 20 mM glycine, 2 M urea and 10 mM dithiothreitol, pH 7.4 using standard methods. A recombinant irrelevant human protein (artemin) produced with an identical epitope tag was also produced for the purpose of screening against antibodies that recognise the tag. Any suitable epitope tag, e.g. ployHis$_6$, polyHis$_8$, polyHQ, etc., and any suitable tagged protein, or the epitope tag alone, can be used for screening to remove antibodies recognising the tag.

Mice, such as Balb/c, are immunized with the ADAM8 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-ADAM8 antibodies.

After a suitable antibody titer has been detected, the animals "positive" for antibodies can be injected with a final intravenous injection of ADAM8. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against ADAM8. Determination of "positive" hybridoma cells secreting the desired monoclonal antibodies against ADAM8 is within the skill in the art.

The positive hybridoma cells can be injected intraperitoneally into syngeneic Balb/c mice to produce ascites containing the anti-ADAM8 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Development of Anti-ADAM8 Monoclonal Antibodies

Ten BALB/c mice (Charles River Laboratories, Wilmington, Del.) were hyperimmunized with purified human ADAM8 in Ribi adjuvant (Ribi Immunochem Research, Inc., Hamilton, Mont.). B-lymphocytes from five of the mice demonstrating the highest anti-ADAM8 antibody titers were harvested from the popliteal and inguinal lymph nodes and fused with mouse myeloma cells (X63.Ag8.653; American Type Culture Collection, Rockville, Md.) as previously described (Kohler et al., 1975). After 8–14 days, the supernatants were harvested and screened for antibody production by direct enzyme-linked immunosorbent assay (ELISA). Sixty-seven positive clones, showing the highest ADAM8-specific immunobinding were expanded for immunocytochemical analysis. Twenty-three of the positive clones were subcloned by limiting dilution. After a second round of subcloning, selected lineages are injected into Pristane-primed mice (Freund and Blair, 1982) for in vivo production of MAb. The resulting ascites fluids are pooled and purified by Protein A affinity chromatography (Pharmacia fast protein liquid chromatography [FPLC]; Pharmacia, Uppsala, Sweden) as previously described (Hongo et al., 1995). The purified antibody preparations are sterile filtered (0.2-µm pore size; Nalgene, Rochester N.Y.) and stored at 4° C. in phosphate buffered saline (PBS).

Direct ELISA for the Selection of Anti-ADAM8 Secreting Hybridomas

Microtiter plates (NUNC) were coated with 100 µl/well of either human ADAM8 or an irrelevant polyHQ tagged protein (1 µg/ml) in 0.05 M carbonate buffer, pH 9.6, overnight at 4° C. The remainder of the assay was performed as previously described (Hongo et al. 1995).

Isotyping

The isotypes of the antibodies were determined using a commercially available isotyping kit (Mouse Antibody Isotyping Kit; dipstick format; Gibco®BRL Life Technologies, Gaithersburg, Md.).

Screening Anti-ADAM8 Secreting Hybridomas for Binding to Fixed Cells

In order to select an anti-ADAM8 secreting hybridoma that will bind specifically to fixed tissues in immunohistochemistry experiments, an assay was developed to screen the hybridomas against fixed cells transfected with an expression vector encoding an ADAM8Ig fusion. Human kidney cells (293 cells) were transfected with an ADAM8Ig expression vector and pRSVneo, a plasmid expressing a gene encoding a protein that confers neomycin resistance. The transfected cells were selected with Geneticin (Gibco®BRL) at 800 ug/ml to specifically select those cells expressing ADAM8. The cells were grown in a 50:50 mix of DMEM:F12 supplemented with 10% FBS and 1× L-Glutamine (Gibco®BRL). These cells were plated in 6 well tissue culture plates (Costar) coated with poly-D-lysine at 2.5 ug/cm$^2$ at about 50% confluence. The next day, the media was aspirated off and the cells were washed twice with PBS (2 ml). The cells were fixed with ice-cold methanol (other fixatives may be used, such as 50:50 methanol:acetone, ethanol, or 10% neutral buffered formalin) for 2 minutes. The cells were washed twice with wash buffer (PBS with 10% FBS). Primary antibody was added to PBS plus 10% FBS and applied to the wells. In this case, the primary antibodies being tested were the secreting hybridomas diluted 1:10 in 1 ml. Incubation was at room temperature for about 2.5 hours with very gentle rotation. The cells were washed five times with wash buffer and a secondary antibody was applied. In this case, the secondary antibody was goat anti-mouse IgG, Fc specific, HRP conjugated (Sigma A0168) diluted 1:5000 in PBS plus 10% FBS. Incubation was again for about 2.5 hours at room temperature with very gentle rotation. Cells were washed five times with wash buffer before applying 2 ml of o-dianisidine saturated ethanol diluted in PBS (50 ml PBS, 0.5 ml o-dianisidine saturated ethanol, 5 ul H$_2$O$_2$). Color development was at room temperature for approximately 1 hour. Cells were washed with H$_2$O twice and plates stored at 4° C. Cells were scored for degree of staining (none, weak, moderate, strong).

Screening Anti-ADAM8 Secreting Hybridomas for Binding to ADAM8Ig

To further evaluate anti-ADAM8 secreting hybridomas, the supernatants were screened in an ELISA utilizing ADAM8 made as an Ig-fusion protein in mammalian cells. A goat anti-human Fc (Caltag H10700) was coated onto 96-well microtiter plates (Nunc Maxisorb) at 2 ug/ml in PBS (50 ul) at 4 degrees C. overnight. The plates were washed in wash buffer (PBS plus 0.05% Tween20) three times. Plates were blocked with 1% BSA in PBS (150 ul) for 1 hour at room temperature. The plates were washed three times with wash buffer. Supernatants from a large scale transient transfection in CHO cells of the construct expressing ADAM8Ig (pRK.ADAM8Ig) were diluted 1:9 in 0.3% BSA in PBS to approximately 500 ng/ml. The diluted supernatants (50 ul) were applied to the plates and incubated for two hours at room temperature. The plates were washed 3 times with wash buffer. Supernatants from anti-ADAM8 secreting hybridomas were applied to the plates (50 ul) neat and incubated at room temperature for 2 hours. Plates were washed three times with wash buffer and a 1:5000 dilution of a goat anti-mouse IgG, Fc specific, HRP conjugated antibody (Sigma A0168) in PBS plus 0.3% BSA was applied for 1 hour at room temperature. Plates were washed three times with wash buffer and color development was with 100 ul TMB Peroxidase Substrate/H$_2$O$_2$ (Kirkegaard and Perry Laboratories) for about 10 minutes. Reactions were stopped with 100ul 1M phosphoric acid. Plates were read on a microplate reader (Molecular Devices) at a wavelength of 450 nm.

From the fusion, 1096-well plates were plated with clones. 67 clones were obtained that were positive in the ELISA with the original immunogen, but negetive in the ELISA with the irrelevant tagged protein. Of these 67 positives, 33 were positive in the ELISA with the supernatant of pRK.ADAM8Ig transiently transfected CHO cells. 23 clones were positive for binding to ADAM8 in a screen against methanol fixed cells. These 23 clones were subcloned. One of these 23 clones was also positive for binding to ADAM8 in a screen against cells fixed in 10% formalin.

Antibodies that bind to cells fixed with methanol or formalin are particularly useful in standard immunohistochemistry experiments to analyze the expression and degree of expression of ADAM8 in sample tissues. Antibodies which recognise and bind to ADAM8 on the surface of living cells and to ADAM8 on fixed cells are particularly interesting since fixing of cells in formalin, for example, is known to alter antigen structures. These antibodies may recognize an epitope on ADAM8 that is retained when the cells/tissue are fixed. Such antibodies may be used clinically as diagnostic reagentts and as therapeutic antibodies.

The foregoing written specification is considered to be sufficient to enable one skilled in the art to practice the invention. Indeed, various modifications of the invention in addition to those shown and described herein will become apparent to those skilled in the art from the foregoing description and fall within the scope of the appended claims.

TABLE 1A

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%.

TABLE 1B

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%.

TABLE 1C

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%.

TABLE 1D

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%.

Table 2A

```
/*
 *
 * C-C increased from 12 to 15
 * Z is average of EQ
 * B is average of ND
 * match with stop is _M; stop-stop = 0; J (joker) match = 0
 */
define   _M    -8        /* value of a match with a stop */ int      _day[26][26] = {
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M, M, M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Table 2B

```
/*
*/
#include <stdio.h>
include <ctype.h> define  MAXJMP   16      /* max jumps in a diag */
define  MAXGAP   24      /* don't continue to penalize gaps larger than this */
#define  JMPS     1024    /* max jmps in an path */
define  MX       4       /* save if there's at least MX-1 bases since last jmp */ define  DMAT     3       /* value of matching bases */
define  DMIS     0       /* penalty for mismatched bases */
#define  DINS0    8       /* penalty for a gap */
#define  DINS1    1       /* penalty per base */
#define  PINS0    8       /* penalty for a gap */
define  PINS1    4       /* penalty per residue */ struct jmp {
        short            n[MAXJMP];    /* size of jmp (neg for dely) */
        unsigned short   x[MAXJMP];    /* base no. of jmp in seq x */
};                                     /* limits seq to 2^16 -1 */ struct diag {
        int        score;      /* score at last jmp */
        long       offset;     /* offset of prev block */
        short      ijmp;       /* current jmp index */
        struct jmp jp;         /* list of jmps */
};

struct path {
        int    spc;            /* number of leading spaces */
        short  n[JMPS];        /* size of jmp (gap) */
        int    x[JMPS];        /* loc of jmp (last elem before gap) */
};

char         *ofile;           /* output file name */
char         *namex[2];        /* seq names: getseqs() */
char         *prog;            /* prog name for err msgs */
char         *seqx[2];         /* seqs: getseqs() */
int          dmax;             /* best diag: nw() */
int          dmax0;            /* final diag */
int          dna;              /* set if dna: main() */
int          endgaps;          /* set if penalizing end gaps */
int          gapx, gapy;       /* total gaps in seqs */
int          len0, len1;       /* seq lens */
int          ngapx, ngapy;     /* total size of gaps */
int          smax;             /* max score: nw() */
int          *xbm;             /* bitmap for matching */
long         offset;           /* current offset in jmp file */
struct diag  *dx;              /* holds diagonals */
struct path  pp[2];            /* holds path for seqs */ char   *calloc(), *malloc(), *index(), *strcpy();
char   *getseq(), *g_calloc();
```

Table 2C

```c
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence wit__ 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)         main
          int        ac;
          char       *av[];
{
          prog = av[0];
          if (ac != 3) {
                     fprintf(stderr,"usage: %s file1 file2\n", prog);
                     fprintf(stderr,"where file1 and file2 are two dna or two protein sequences.\n");
                     fprintf(stderr,"The sequences can be in upper- or lower-case\n");
                     fprintf(stderr,"Any lines beginning with ';' or '<' are ignored\n");
                     fprintf(stderr,"Output is in the file \"align.out\"\n");
                     exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

endgaps = 0;                    /* 1 to penalize endgaps */
          ofile = "align.out";            /* output file */ nw();                /* fill in the matrix, get the possible jmps */
          readjmps();          /* get the actual jmps */
          print();             /* print stats, alignment */ cleanup(0);          /* unlink any tmp files */
}
```

Table 2D

```c
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()    nw
{
        char        *px, *py;       /* seqs and ptrs */
        int         *ndely, *dely;  /* keep track of dely */
        int         ndelx, delx;    /* keep track of delx */
        int         *tmp,           /* for swapping row0, row1 */
        int         mis;            /* score for each type */
        int         ins0, ins1;     /* insertion penalties */
        register    id;             /* diagonal index */
        register    ij;             /* jmp index */
        register    *col0, *col1;   /* score for curr, last row */
        register    xx, yy;         /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely",  len1+1, sizeof(int));
        col0  = (int *)g_calloc("to get col0",  len1+1, sizeof(int));
        col1  = (int *)g_calloc("to get col1",  len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;        /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;      }
```

Table 2E

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 2F

...nw

```
                id = xx - yy + len1 - 1;
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                                && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0,
                                                dx[id].offset = offset;
                                                offset += sizeof(struct jmp) + sizeof(offset);
                                        }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;

if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
}
(void) free((char *)ndely),
(void) free((char *)dely);
(void) free((char *)col0);
```

```
        (void) free((char *)col1);
}       Page 4 of nw.c
```

Table 2G
```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC      3
#define P_LINE   256    /* maximum output line */
define P_SPC    3      /* space between name or num and seq */ extern    _day[26][26];
int       olen;         /* set output line length */
FILE      *fx;          /* output file */ print()   print
{
          int     lx, ly, firstgap, lastgap;    /* overlap */ if ((fx = fopen(ofile, "w")) == 0) {
                    fprintf(stderr,"%s: can't write %s\n", prog, ofile);
                    cleanup(1);
          }
          fprintf(fx, "<first sequence: %s (length = %d)\n", namex[0], len0);
          fprintf(fx, "<second sequence: %s (length = %d)\n", namex[1], len1);
          olen = 60;
          lx = len0;
          ly = len1;
          firstgap = lastgap = 0;
          if (dmax < len1 - 1) {          /* leading gap in x */
                    pp[0].spc = firstgap = len1 - dmax - 1;
                    ly -= pp[0].spc;
          }
          else if (dmax > len1 - 1) {     /* leading gap in y */
                    pp[1].spc = firstgap = dmax - (len1 - 1);
                    lx -= pp[1].spc;
          }
          if (dmax0 < len0 - 1) {         /* trailing gap in x */
                    lastgap = len0 - dmax0 -1;
                    lx -= lastgap;
          }
          else if (dmax0 > len0 - 1) {    /* trailing gap in y */
                    lastgap = dmax0 - (len0 - 1);
                    ly -= lastgap;
          }
          getmat(lx, ly, firstgap, lastgap);
          pr_align();
}
```

Table 2H

```c
/*
 * trace back the best path, count matches
 */
static
getmat(lx, ly, firstgap, lastgap)        getmat
        int     lx, ly;                  /* "core" (minus endgaps) */
        int     firstgap, lastgap;       /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

Page 2 of nwprint.c

Table 21

```
fprintf(fx, "<gaps in first sequence: %d", gapx);   ...getmat
if (gapx) {
        (void) sprintf(outx, " (%d %s%s)",
                ngapx, (dna)? "base":"residue", (ngapx == 1)? "":"s");
        fprintf(fx,"%s", outx);

fprintf(fx, ", gaps in second sequence: %d", gapy);
if (gapy) {
        (void) sprintf(outx, " (%d %s%s)",
                ngapy, (dna)? "base":"residue", (ngapy == 1)? "":"s");
        fprintf(fx,"%s", outx),
}
if (dna)
        fprintf(fx,
        "\n<score: %d (match = %d, mismatch = %d, gap penalty = %d + %d per base)\n",
        smax, DMAT, DMIS, DINS0, DINS1);
else
        fprintf(fx,
        "\n<score: %d (Dayhoff PAM 250 matrix, gap penalty = %d + %d per residue)\n",
        smax, PINS0, PINS1);
if (endgaps)
        fprintf(fx,
        "<endgaps penalized. left endgap: %d %s%s, right endgap: %d %s%s\n",
        firstgap, (dna)? "base" : "residue", (firstgap == 1)? "" : "s",
        lastgap, (dna)? "base" : "residue", (lastgap == 1)? "" : "s");
else
        fprintf(fx, "<endgaps not penalized\n");
} static          nm;                     /* matches in core -- for checking */
static          lmax;                   /* lengths of stripped file names */
static          ij[2];                  /* jmp index for a path */
static          nc[2];                  /* number at start of current line */
static          ni[2];                  /* current elem number -- for gapping */
static          siz[2];
static char     *ps[2];                 /* ptr to current element */
static char     *po[2];                 /* ptr to next output char slot */
static char     out[2][P_LINE];         /* output line */
static char     star[P_LINE];           /* set by stars() */

/*
* print alignment of described in struct path pp[]
*/
static
pr_align()pr_align
{
        int             nn;     /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
```

}

Table 2J

```
for (nn = nm = 0, more = 1; more; ) {    ...pr_align
        for (i = more = 0; i < 2; i++) {
                /*
                 * do we have more of this sequence?
                 */
                if (!*ps[i])
                        continue;

more++;

if (pp[i].spc) {       /* leading space */
                        *po[i]++ = ' ';
                        pp[i].spc--;
                }
                else if (siz[i]) {     /* in a gap */
                        *po[i]++ = '-';
                        siz[i]--;
                }
                else {                 /* we're putting a seq element
                                        */
                        *po[i] = *ps[i];
                        if (islower(*ps[i]))
                                *ps[i] = toupper(*ps[i]);
                        po[i]++;
                        ps[i]++;

/*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
  }
}
/*
 * dump a block of lines, including numbers, stars: pr_align()
 */
static
dumpblock()       dumpblock
{
        register i;

for (i = 0; i < 2; i++)
                *po[i]-- = '\0';
```

P1773R1

Page 4 of nwprint.c

Table 2K

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star),
                                if (i == 1)
                                        nums(i);
                        }
                }
}

/*
 * put out a number line: dumpblock()
 */
static
nums(ix) nums
        int     ix;        /* index in out[] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
 * put out a line (name, [num], seq, [num]): dumpblock()
 */
static
putline(ix)         putline
        int     ix;
{
```

P1773R1

Page 5 of nwprint.c

Table 2L

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()   stars
{
        int             i;
        register char   *p0, *p1, cx, *px;

if (!*out[0] || (*out[0] == ' ' && *(po[0]) == ' ') ||
           !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Page 6 of nwprint.c

Table 2M

```
/*
 * strip path or prefix from pn, return len: pr_align()
 */
static
stripname(pn)          stripname
        char    *pn;   /* file name (may be path) */
{
        register char    *px, *py;

py = 0;
        for (px = pn; *px; px++)
                if (*px == '/')
                        py = px + 1;
        if (py)
                (void) strcpy(pn, py);
        return(strlen(pn));

}
```

Table 2N

```c
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";         /* tmp file for jmps */
FILE    *fj;

int     cleanup();                          /* cleanup tmp file */
long    lseek();

/*
 * remove any tmp file if we blow
 */
cleanup(i)      cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)       getseq
        char    *file;          /* file name */
        int     *len;           /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

P1773R1

Page 1 of nwsubr.c

Table 20

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
} char    *
g_calloc(msg, nx, sz)      g_calloc
        char    *msg;           /* program, calling routine */
        int     nx, sz;         /* number and size of elements */
{
        char    *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
 * get final jmps from dx[] or tmp file, set pp[], reset dmax: main()
 */
readjmps()              readjmps
{
        int     fd = -1;
        int     siz, i0, i1;
        register i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

P1773R1

Table 2P

...readjmps

```
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].jmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {                  /* gap in second seq */
                                pp[1].n[i1] = -siz;
                                xx += siz;

/* id = xx - yy + len1 - 1
                                 */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) {     /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }

/* reverse the order of jmps
         */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;
        }
        for (j = 0, i1--; j < i1; j++, i1--) {
                i = pp[1].n[j]; pp[1].n[j] = pp[1].n[i1]; pp[1].n[i1] = i;
                i = pp[1].x[j]; pp[1].x[j] = pp[1].x[i1]; pp[1].x[i1] = i;
        }
        if (fd >= 0)
                (void) close(fd);
        if (fj) {
                (void) unlink(jname);
                fj = 0;
                offset = 0;
```

}

}

Table 2Q

```
/*
 * write a filled jmp struct offset of the prev one (if any): nw()
 */
writejmps(ix)           writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

What is claimed is:

1. A method for inhibiting tumor cell growth comprising: exposing tumor cells selected from the group consisting of breast, colon, and lung tumor cells that overexpress ADAM8 to an antibody or fragment thereof that binds ADAM8 polypeptide having the sequence of SEQ ID NO:1, wherein said antibody or antibody fragment is conjugated to a cytotoxic agent; and wherein said exposure inhibits growth of said tumor cells.

2. The method of claim 1, wherein the cytotoxic agent comprises a radioactive isotope.

3. The method of claim 2, wherein the radioactive isotope is $^{212}$Bi, $^{131}$I, $^{131}$In, $^{90}$Y, $^{186}$Re, or a combination thereof.

4. The method of claim 1, wherein the cytotoxic agent comprises a chemotherapeutic agent.

5. The method of claim 4, wherein the chemotherapeutic agent adriamycin, doxorubicin, epirubicin, 5-fluorouracil, cytosine arabinoside, cyclophosphamide, thiotepa, busulfan, cytoxin, paclitaxel, doxetaxel, toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins, 5-FU, 6-thioguanine, 6-mercaptopurine, actinomycin D, VP-16, chlorambucil, melphalan, or a combination thereof.

6. The method of claim 1, wherein the cytotoxic agent comprises a toxin.

7. The method of claim 6, wherein the toxin is diphtheria A chain, a nonbinding active fragment of diphtheria toxin, a nonbinding active fragment of cholera toxin, a nonbinding active fragment of botulin toxin, *Pseudomonas aeruginosa* exotoxin A chain, ricin A chain, abrin A chain, modeccin A chain, alpha-sarcin, *Aleurites fordii* proteins, dianthin proteins, *Phytolaca americana* proteins PAPI, PAPII, PAP-S, *Momordica charantia* inhibitor, curcin, crotin, *Sapaonaria officinalis* inhibitor, gelonin, saporin, mitogellin, restrictocin, phenomycin, enomycin, tricothecenes, calicheamicins, maytansinoids, palytoxin, CC1065, or a combination thereof.

8. The method of claim 1, wherein said exposure to said conjugate is in combination with exposure to one or more additional chemotherapeutic agent and/or radiation.

9. The method of claim 1, wherein said antibody is a monoclonal antibody.

10. The method of claim 1, wherein said antibody is a humanized antibody.

11. The method of claim 1, wherein said antibody is a bispecific antibody.

12. The method of claim 1, wherein said fragment is a Fv, SFv, Fab, Fab', or F(ab')$_2$.

* * * * *